US012760313B2

(12) United States Patent
Bayer et al.

(10) Patent No.: US 12,760,313 B2
(45) Date of Patent: Oct. 13, 2026

(54) MODIFIED TOMATO PLANTS WITH EXTENDED SHELF LIFE

(71) Applicant: Sound Agriculture Company, Emeryville, CA (US)

(72) Inventors: Travis Bayer, San Francisco, CA (US); Jennifer Samson, Oakland, CA (US); Eric Davidson, Houston, TX (US); Shaneece Flores Gonzales, Berkeley, CA (US); Jack Colicchio, Berkeley, CA (US); Alex Greenlon, San Pablo, CA (US)

(73) Assignee: DECIBEL BIO, INC., Berkeley, CA (US)

( * ) Notice: Subject to any disclaimer, the term of this patent is extended or adjusted under 35 U.S.C. 154(b) by 428 days.

(21) Appl. No.: 17/810,517

(22) Filed: Jul. 1, 2022

(65) Prior Publication Data

US 2023/0058857 A1 Feb. 23, 2023

Related U.S. Application Data

(60) Provisional application No. 63/218,225, filed on Jul. 2, 2021.

(51) Int. Cl.
*C12N 15/82* (2006.01)

(52) U.S. Cl.
CPC ..... *C12N 15/8242* (2013.01); *C12N 15/8216* (2013.01)

(58) Field of Classification Search
None
See application file for complete search history.

(56) References Cited

U.S. PATENT DOCUMENTS

| | | | |
|---|---|---|---|
| 5,795,782 | A | 8/1998 | Church et al. |
| 9,288,952 | B2 | 3/2016 | Sisson |
| 10,813,311 | B2 | 10/2020 | Kramer |
| 11,591,608 | B2 | 2/2023 | Bayer et al. |
| 11,812,738 | B2 | 11/2023 | Sammons et al. |
| 12,203,083 | B2 | 1/2025 | Bayer et al. |
| 2005/0026160 | A1 | 2/2005 | Allerson et al. |
| 2018/0163219 | A1 | 6/2018 | Huang et al. |
| 2019/0024086 | A1 | 1/2019 | Lande et al. |
| 2019/0055555 | A1 | 2/2019 | Hauser |
| 2023/0054672 | A1 | 2/2023 | Berry et al. |

FOREIGN PATENT DOCUMENTS

| | | | |
|---|---|---|---|
| CN | 107714685 A | 2/2018 |
| CN | 109890962 A | 6/2019 |
| JP | 2013535212 A | 9/2013 |
| WO | 2010001909 A1 | 1/2010 |
| WO | 2012018754 A2 | 2/2012 |
| WO | 2014106837 A2 | 7/2014 |
| WO | 2014106838 A2 | 7/2014 |
| WO | 2020191072 | 9/2020 |

OTHER PUBLICATIONS

Shinozaki, Yoshihito, et al. "High-resolution spatiotemporal transcriptome mapping of tomato fruit development and ripening." Nature communications 9.1 (2018): 364. (Year: 2018).*
Wang, Sumei, Wanyin Wu, and Francois X. Claret. "Mutual regulation of microRNAs and DNA methylation in human cancers." Epigenetics 12.3 (2017): 187-197. (Year: 2017).*
Martienssen, Robert A., and Vincent Colot. "DNA methylation and epigenetic inheritance in plants and filamentous fungi." Science 293.5532 (2001): 1070-1074. (Year: 2001).*
Chi, Ming, et al. "Reduced polyphenol oxidase gene expression and enzymatic browning in potato (*Solanum tuberosum* L.) with artificial microRNAs." BMC Plant Biology 14 (2014): 1-18. (Year: 2014).*
O'Brien, Jacob, et al. "Overview of microRNA biogenesis, mechanisms of actions, and circulation." Frontiers in endocrinology 9 (2018): 402. (Year: 2018).*
Ecker, Joseph R. "Epigenetic trigger for tomato ripening." Nature biotechnology 31.2 (2013): 119-120. (Year: 2013).*
Zhang, Lincheng, et al. "The SIFSR gene controls fruit shelf-life in tomato." Journal of Experimental Botany 69.12 (2018): 2897-2909. (Year: 2018).*
PCT/US2022/073384 , "International Preliminary Report on Patentability", Jan. 11, 2024, 11 pages.
Application No. PCT/US2022/073384 , International Search Report and Written Opinion, Mailed On Oct. 14, 2022, 15 pages.
"Solanum Lycopersicum Chromosome Ch07, Complete Genome", NCBI, GenBank: HG975519.1., Nov. 17, 2015, 1 page.
Ecker, "Epigenetic Trigger for Tomato Ripening", Nature Biotechnology, vol. 31, No. 2, Feb. 2013, pp. 1-4.
Liu et al., "SIGRAS4 Accelerates Fruit Ripening by Regulating Ethylene Biosynthesis Genes and SIMADS1 in Tomato", Horticulture Research., vol. 8, No. 3, Jan. 1, 2021, pp. 1-11.
Zhang et al., "The SIFSR Gene Controls Fruit Shelf-Life in Tomato", Journal of Experimental Botany, vol. 69, No. 12, Apr. 4, 2018, pp. 2897-2909.

(Continued)

*Primary Examiner* — Amjad Abraham
*Assistant Examiner* — Kelsey L McWilliams
(74) *Attorney, Agent, or Firm* — Kilpatrick Townsend & Stockton LLP

(57) ABSTRACT

Provided herein are modified tomato plants comprising an introduced modification of genomic DNA at the SlFSR gene or a transcription regulatory region thereof. In some instances, the introduced modification is heritable. In some instances, the introduced modification is an epigenetic such as hypermethylation. Also provided are progeny plants produced from the modified tomato plants, tomato seeds and tomato fruit produced by the modified tomato plants or progeny plants. Also provided are methods of making and growing the modified tomato plant and obtaining modified tomato fruit as well as nucleic acid reagents useful in the methods.

31 Claims, 8 Drawing Sheets

Specification includes a Sequence Listing.

(56) References Cited

OTHER PUBLICATIONS

"In re Herz", Casetext: Smarter Legal Research, 537 F.2d 549, 551-52, 190 U.S.P.Q. 461, 463 (CCPA 1976), Jul. 22, 1976, pp. 1-4.
Altschul et al., "Basic Local Alignment Search Tool", Journal of Molecular Biology, vol. 215, 1990, pp. 403-410.
Ashapkin et al., "Epigenetic variability in plants: Heritability, adaptability, evolutionary significance", Russian Journal of Plant Physiology, vol. 63, 2016, pp. 181-192.
Batzer et al., "Enhanced Evolutionary PCR Using Oligonucleotides with Inosine at the 3'-Terminus", Nucleic Acids Research, vol. 19, No. 18, Sep. 25, 1991, p. 5081.
Karlin et al., "Applications and Statistics for Multiple High-Scoring Segments in Molecular Sequences", Proceedings of the National Academy of Sciences USA, vol. 90, No. 12, Jun. 15, 1993, pp. 5873-5877.
Krueger et al., "Bismark: A Flexible Aligner and Methylation Caller for Bisulfite-Seq Applications", Bioinformatics, vol. 27, No. 11, Jun. 1, 2011, pp. 1571-1572.
Mahajan et al., "Postharvest treatments of fresh produce", Philos Trans A Math Phys Eng Sci., 372, 2017, 19 pages.
Nambeesan et al., "Overexpression of yeast spermidine synthase impacts ripening, senescence and decay symptoms in tomato", The Plant Journal, 63(5), Sep. 2010, pp. 836-847.
Rossolini et al., "Use of Deoxyinosine-containing Primers Vs Degenerate Primers for Polymerase Chain Reaction Based on Ambiguous Sequence Information", Molecular and Cellular Probes, vol. 8, No. 2, Apr. 1994, pp. 91-98.
Sambrook et al., "Molecular Biology: A Laboratory Approach", Cold Spring Harbor, N.Y, 1989, 18 pages.
Smith et al., "Comparison of Biosequences", Advances in Applied Mathematics, vol. 2, No. 4, Dec 1981, pp. 482-489.
Zhang et al., "The SlFSR gene controls fruit shelf-life in tomato", Journal of Experimental Botany, vol. 69, No. 12, 2018, pp. 2897-2909.
Aufsatz , et al., "RNA-directed DNA Methylation in *Arabidopsis*", Proceedings of the National Academy of Sciences, vol. 99, No. 4, Dec. 10, 2002, pp. 16499-16506.
Bhagwat , et al., "An in Vivo Transient Expression System can be Applied for Rapid and Effective Selection of Artificial MicroRNA Constructs for Plant Stable Genetic Transformation", Journal of Genetics and Genomics, vol. 40, No. 5, May 20, 2013, pp. 261-270.
Chi , et al., "Reduced Polyphenol Oxidase Gene Expression and Enzymatic Browning in Potato (*Solanum tuberosum* L.) with Artificial MicroRNAs", BMC Plant Biology, vol. 14, No. 62, Mar. 11, 2014, pp. 1-18.
Finnegan , et al., "DNA Methylation in Plants", Annual Review of Plant Physiology and Plant Molecular Biology, vol. 49, Jun. 1998, pp. 223-247.
Gebala , et al., "Quantitative Studies of an RNA Duplex Electrostatics by Ion Counting", Biophysical Journal, vol. 117, Sep. 17, 2019, pp. 1116-1124.
Hermann , et al., "RNA Bulges as Architectural and Recognition Motifs", Structure, vol. 8, No. 3, Mar. 15, 2000, pp. R47-R54.
Horesh , et al., "A Rapid Method for Detection of Putative RNAi Target Genes in Genomic Data", Bioinformatics, vol. 19, Nov. 2003, pp. ii73-ii80.
Lennox , et al., "Chemical Modification and Design of Anti-miRNA Oligonucleotides", Gene Therapy, vol. 18, No. 12, Jul. 14, 2011, pp. 1111-1120.
Ma , et al., "Angiosperms Are Unique among Land Plant Lineages in the Occurrence of Key Genes in the RNA-Directed DNA Methylation (RdDM) Pathway", Genome Biology and Evolution, vol. 7, No. 9, Sep. 2, 2015, pp. 2648-2662.
Marienssen , et al., "DNA Methylation and Epigenetic Inheritance in Plants and Filamentous Fungi", Science, vol. 293, No. 5532, Aug. 10, 2001, pp. 1070-1074.
MX/A/2023/015505 , "Office Action", Apr. 1, 2024, 2 pages.
Richmond , et al., "The Structure of DNA in the Nucleosome Core", Nature, vol. 423, May 8, 2003, pp. 145-150.
Smalheiser , et al., "Mammalian Argonaute-DNA Binding?", Biology Direct, vol. 9, No. 27, Dec 2014, pp. 1-11.
Tanaka , et al., "A'-form RNA Double helix in the Single Crystal Structure of r(UGAGCUUCGGCUC)", Nucleic Acids Research, vol. 27, No. 4, Feb. 15, 1999, pp. 949-955.
Wang , et al., "Mutual Regulation of MicroRNAs and DNA Methylation in Human Cancers", Epigenetics, vol. 12, No. 3, Mar. 4, 2017, pp. 187-197.
Xie , et al., "siRNA-Directed DNA Methylation in Plants", Current Genomics, vol. 16, No. 1, Feb. 2015, pp. 23-31.
Yoshizumi , et al., "Selective Gene Delivery for Integrating Exogenous DNA into Plastid and Mitochondrial Genomes Using Peptide-DNA Complexes", Biomacromolecules, vol. 19, No. 15, Mar. 30, 2018, pp. 1582-1591.
Yu , et al., "Methylation as a Crucial Step in Plant MicroRNA Biogenesis", Science, vol. 307, No. 5711, Feb. 11, 2005, pp. 932-935.
Zhang , et al., "Dynamics and Function of DNA Methylation in Plants", Nature Reviews: Molecular Cell Biology, vol. 19, Aug. 2018, pp. 489-506.
EP20773409.6 , "Extended European Search Report", Nov. 17, 2022, 6 pages.
PCT/US2020/023391 , "International Search Report and Written Opinion", Jul. 6, 2020, 10 pages.
Ito, et al. "DNA-binding specificity, transcriptional activation potential, and the rin mutation effect for the tomato fruit-ripening regulator RIN." The Plant Journal 55.2, Jul. 2008, pp. 212-223.
Ito, et al. "Allelic mutations in the ripening-inhibitor locus generate extensive variation in tomato ripening." Plant physiology 183.1, May 2020, pp. 80-95.
Matzke et al., "RNA-directed DNA Methylation: An Epigenetic Pathway of Increasing Complexity", Nature Reviews Genetics, vol. 15, No. 6, Jun. 2014, pp. 394-408.
Ramachandran et al., "Small RNA metabolism in *Arabidopsis*", Trends in Plant Science, vol. 13, No. 7, pp. 368-374, Jan. 5, 2026.

* cited by examiner

MODIFIED TOMATO PLANTS WITH EXTENDED SHELF LIFE

CROSS-REFERENCE TO RELATED APPLICATIONS

This application claims priority to U.S. Provisional Application No. 63/218,225, filed on Jul. 2, 2021, the entire disclosure of which is herein incorporated by reference for all purposes.

REFERENCE TO A SEQUENCE LISTING

The official copy of the sequence listing is submitted electronically via Patent Center as an XML formatted sequence listing with a file named 1335135_seglist.xml, created on Jul. 1, 2022, and having a size of 120,712 bytes, and is filed concurrently with the specification. The sequence listing contained in this XML formatted document is part of the specification and is herein incorporated by reference in its entirety.

BACKGROUND

Tomatoes are well-established as a commercially important fruit product. Nearly 200 million metric tons of tomatoes are produced yearly worldwide and sold as fresh or processed fruit. The industry faces the challenge of limited shelf life for tomatoes sold fresh. Over 3.1% of fresh tomatoes bought by U.S. households are thrown out, at an estimated cost of over $2.3 billion per year. Adding to the challenge is the popularity of heirloom tomato varieties, which are often preferred by consumers for their superior flavor, but which display shortened shelf life and fragile fruits. As such, there is a need for tomato plants that produce fruit with extended shelf life.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

The present disclosure is based, in part, on the creation by the inventors of modified tomato plants that produce fruit displaying extended shelf life relative to unmodified tomato plants. In some embodiments, the modified tomato plants comprise an introduced modification at the SlFSR gene or a transcription regulatory region thereof. In some embodiments, the modified tomato plants comprise tomato variety SND-017, as described herein. In some embodiments, the introduced modification is epigenetic, e.g., hypermethylation of genomic DNA. In some embodiments, the introduced modification is heritable.

In one aspect, provided is a modified tomato plant comprising an introduced modification comprising hypermethylation of genomic DNA at a SlFSR gene or a transcription regulatory region thereof. In some embodiments, the introduced modification is heritable. In some embodiments, the hypermethylation is within a 1 kb region upstream of the translation start site of the SlFSR gene. In some embodiments, the hypermethylation is within a 0.5 kb region upstream of the translation start site of the SlFSR gene. In some embodiments, the modified tomato plant has a reduced expression level of a gene product encoded by the SlFSR gene. In some embodiments, the gene product is an mRNA transcript or a protein. In some embodiments, the expression level of the gene product is reduced relative to the expression level of the gene product encoded by the SlFSR gene in an unmodified tomato plant. In some embodiments, the modified tomato plant is of an heirloom variety. In some embodiments, the modified tomato plant is of a Brandywine variety. In some embodiments, the modified tomato plant is of a Micro Tom variety. In some embodiments, the modified tomato plant is an offspring of the modified tomato plant.

In another aspect, provided is a modified tomato fruit produced by the modified tomato plant or an offspring thereof. In some embodiments, the modified tomato fruit has an extended shelf life relative to a tomato fruit produced from an unmodified tomato plant. In some embodiments, the modified tomato fruit retains at least a pre-determined minimum degree of firmness of for at least 14 days. In some embodiments, the modified tomato fruit retains at least a pre-determined minimum degree of for at least 1.3 times as long as an unmodified tomato fruit. In some embodiments, the modified tomato fruit retains an increased degree of firmness relative to an unmodified tomato fruit harvested at the same time at least 7 days after harvesting. In some embodiments, the modified tomato fruit has increased water content relative to an unmodified tomato fruit harvested at the same time at least 7 days after harvesting. In some embodiments, the modified tomato fruit further comprises a coating that reduces ethylene release from the modified tomato fruit or absorbs ethylene released from the modified tomato fruit. In some embodiments, the modified tomato fruit is stored in a climate-controlled environment at a temperature between about 8° C. and about 24° C.

In another aspect, provided is a modified tomato seed produced by the modified tomato plant or offspring thereof. Also provided is a plant produced by growing the modified tomato seed. Also provided is a plant part of any of the plants described above. In some embodiments, the plant part is a leaf, pollen, an ovule, a fruit, a scion, a rootstock, or a cell. In some embodiments, the plant part is a fruit.

In yet another aspect, provided is an isolated or cultured cell of the modified tomato plant or offspring thereof, the modified tomato fruit, or the modified tomato seed. In some embodiments, the isolated or cultured cell is from an embryo, a meristem, a cotyledon, a pollen, a leaf, an anther, a root, a root tip, a pistil, a flower, a seed, and/or a stalk. In some embodiments, the cell is a protoplast. Also provided is a population of cells comprising a plurality of the isolated or cultured cells.

In another aspect, provided is a method for growing a modified tomato plant, the method comprising growing in a field or an area of cultivation a modified tomato plant of any one of example(s)s 1 to 9 or a seed or seedling thereof.

In another aspect, provided is a method for producing a modified tomato fruit, the method comprising growing in a field or an area of cultivation a modified tomato plant of anyone of example(s)s 1 to 9 or a seed or seedling thereof to produce a modified tomato plant and cultivating the modified tomato plant to produce a modified tomato fruit. In some embodiments, the method further comprises harvesting the modified tomato fruit from the modified tomato plant.

In another aspect, provided is a method for producing the modified tomato plant as described above, the method comprising: applying a formulation comprising at least one (e.g., a plurality) of artificial nucleic acid constructs to a tomato seed, a tomato plant, a constituent of a tomato plant, or any combination thereof, each artificial nucleic acid construct comprising a double stranded oligonucleotide comprising: (a) a first strand having a length of 20 to 30 nucleotides or nucleosides or a combination thereof and comprising at least 90% identity to a portion of the SlFSR gene or a transcription regulatory region thereof; (b) a second strand having a length of 20 to 30 nucleotides or nucleosides or a combination thereof that is complementary to at least a portion of the first strand; (c) a terminal end overhang; and (d) a ribose modified at a 2' or 3' position, or a deoxyribose modified at a 2' or 3' position, or a combination thereof, wherein the at least one (e.g., the plurality) artificial nucleic acid construct penetrates the tomato seed, the tomato plant, the constituent of a tomato plant, or any combination thereof and specifically hybridizes to genomic DNA of the tomato seed, the tomato plant, the constituent of a tomato plant, or any combination thereof; and cultivating the tomato seed, the tomato plant, the constituent of a tomato plant, or any combination thereof with the formulation applied for a period of time sufficient to produce the hypermethylation of the genomic DNA of the SlFSR gene or a transcription regulatory region thereof. In some embodiments, the formulation is applied to a tomato seed. In some embodiments, the tomato seed is from a modified tomato plant comprising an introduced modification (e.g., an introduced heritable modification) comprising hypermethylation of genomic DNA at a SlFSR gene or a transcription regulatory region thereof. In some embodiments, the formulation is a powder, granule, pellet, bead, or liquid. In some embodiments, the formulation is a liquid. In some embodiments, the first strand and the second strand are the same length. In some embodiments, the terminal end overhang is a 3' end overhang. In some embodiments, the artificial nucleic acid construct comprises two 3' end overhangs. In some embodiments, the ribose modified at a 2' or 3' position, or the deoxyribose modified at a 2' or 3' position, or the combination thereof are at a terminal nucleotide or nucleoside of the first strand or the second strand of the artificial nucleic acid construct. In some embodiments, the ribose modified at a 2' or 3' position, or the deoxyribose modified at a 2' or 3' position, or the combination thereof are at a 3' terminal nucleotide or nucleoside of the first strand and the second strand of the artificial nucleic acid construct. In some embodiments, the ribose modified at a 2' or 3' position, or the deoxyribose modified at a 2' or 3' position, or the combination thereof comprises a 2'-O—R group. In some embodiments, the 2'-O—R group is selected from the group consisting of: an alkyl, an aryl, a haloalkyl, an amino, a methyl, an acetyl, and a halo. In some embodiments, the 2'-O—R group is a methyl. In some embodiments, the first strand comprises at least 90% identity to a portion of a transcription regulatory region of the SlFSR gene within a 1.0 kb region upstream of the translation start site of the SlFSR gene. In some embodiments, the first strand comprises at least 90% identity to a portion of a transcription regulatory region of the SlFSR gene within a 0.5 kb region upstream of the translation start site of the SlFSR gene. In some embodiments, the first strand and/or the second strand comprises a sequence with at least 90% identity to any of SEQ ID NOs: 1-82. In some embodiments, the first strand and/or the second strand comprises a sequence with at least about 30% guanine cytosine (GC) content. In some embodiments, the method comprises applying a formulation comprising a plurality of artificial nucleic acid constructs to the tomato seed, the tomato plant, the constituent of a tomato plant, or any combination thereof. In some embodiments, the plurality of artificial nucleic acid constructs comprises at least some artificial nucleic acid constructs having a first strand comprising at least 90% identity to different portions of the SlFSR gene or a transcription regulatory region thereof. In some embodiments, each artificial nucleic acid construct in the plurality of artificial nucleic acid constructs has a first strand comprising at least 90% identity to a different portion of the SlFSR gene or a transcription regulatory region thereof.

In another aspect, provided is an artificial nucleic acid construct comprising a double stranded oligonucleotide comprising: (a) a first strand having a length of 20 to 30 nucleotides or nucleosides or a combination thereof and comprising at least 90% identity to a portion of the SlFSR gene or a transcription regulatory region thereof; (b) a second strand having a length of 20 to 30 nucleotides or nucleosides or a combination thereof that is complementary to at least a portion of the first strand; (c) a terminal end overhang; and (d) a ribose modified at a 2' or 3' position, or a deoxyribose modified at a 2' or 3' position, or a combination thereof. In some embodiments, the first strand and the second strand are the same length. In some embodiments, the terminal end overhang is a 3' end overhang. In some embodiments, the artificial nucleic acid construct comprises two 3' end overhangs. In some embodiments, the ribose modified at a 2' or 3' position, or the deoxyribose modified at a 2' or 3' position, or the combination thereof are at a terminal nucleotide or nucleoside of the first strand and/or the second strand of the artificial nucleic acid construct. In some embodiments, the ribose modified at a 2' or 3' position, or the deoxyribose modified at a 2' or 3' position, or the combination thereof are at a 3' terminal nucleotide or nucleoside of the first strand and the second strand of the artificial nucleic acid construct. In some embodiments, the ribose modified at a 2' or 3' position, or the deoxyribose modified at a 2' or 3' position, or the combination thereof comprises a 2'-O—R group. In some embodiments, the 2'-O—R group is selected from the group consisting of: an alkyl, an aryl, a haloalkyl, an amino, a methyl, an acetyl, and a halo. In some embodiments, the 2'-O—R group is a methyl. In some embodiments, the first strand comprises at least 90% identity to an SlFSR transcription regulatory region within a 1.0 kb region upstream of the translation start site of the SlFSR gene. In some embodiments, the first strand comprises at least 90% identity to an SlFSR transcription regulatory region within a 0.5 kb region upstream of the translation start site of the SlFSR gene. In some embodiments, the first strand and/or the second strand comprises a sequence with at least 90% identity to any of SEQ ID NOs: 1-82. In some embodiments, the first strand and/or the second strand comprises a sequence with at least about 30% guanine cytosine (GC) content.

In another aspect, provided is a plurality of artificial nucleic acid constructs comprising at least about 2-125 of the artificial nucleic acid constructs. In some embodiments, the plurality of artificial nucleic acid constructs comprises at least 2-50 of the artificial nucleic acid constructs. In some embodiments, the plurality of artificial nucleic acid constructs comprises at least some artificial nucleic acid constructs having a first strand comprising at least 90% identity to different portions of the SlFSR gene or a transcription regulatory region thereof. In some embodiments, each artificial nucleic acid construct in the plurality has a first strand comprising at least 90% identity to a different portion of the SlFSR gene or a transcription regulatory region thereof.

In another aspect, provided is a formulation comprising at least one artificial nucleic acid construct as described above. In another aspect, provided is a formulation comprising a plurality of artificial nucleic acid constructs as described above. In some embodiments, formulation is a powder, granule, pellet, bead, or liquid. In some embodiments, formulation is a liquid. In some embodiments, each of the artificial nucleic acid constructs in the plurality are present in the formulation at a concentration of about 250 μM.

In another aspect, provided is a composition comprising a) a formulation as described above and b) a tomato seed, a tomato plant, a constituent of a tomato plant, or any combination thereof.

In another aspect, provided herein are seeds of tomato plant variety SND-017. Also provided are plants produced by growing the seeds. Also provided plant parts of the plants. In some embodiments, the plant part is a leaf, pollen, an ovule, a fruit, a scion, a rootstock, or a cell. In some embodiments, the plant part is a fruit. Also provided are tomato plants, and parts thereof, having all or essentially all the physiological and morphological characteristics of the plants described above.

In another aspect, provided herein are isolated or cultured cells of the plants described above. In some embodiments, the cells are from an embryo, a meristem, a cotyledon, a pollen, a leaf, an anther, a root, a root tip, a pistil, a flower, a seed, and/or a stalk. In some embodiments, the cells are protoplasts. Also provided are populations of cells comprising a plurality of the isolated or cultured cells. Also provided are tomato plants regenerated form any of the isolated or cultured cells described above.

In another aspect, provided herein are methods of vegetatively propagating any of the plants described herein, the methods comprising the steps of: (a) collecting tissue capable of being propagated from the plant; (b) cultivating said tissue to obtain proliferated shoots; and (c) rooting said proliferated shoots to obtain rooted plantlets. In some embodiments, the methods further comprise growing plants from said rooted plantlets.

In another aspect, provided herein are methods of producing a tomato plant, comprising crossing any of the plants described above with a second tomato plant one or more times, and selecting progeny from said crossing.

In another aspect, provided herein are methods of introducing a desired trait into a tomato variety comprising: (a) crossing a first plant according to any of the plants described above with a tomato plant that comprises a desired trait to produce F1 progeny; (b) selecting an F1 progeny that comprises the desired trait; (c) crossing the selected F1 progeny with a second plant according to any of the plants described above to produce backcross progeny; (d) selecting backcross progeny comprising the desired trait and all or essentially all the physiological and morphological characteristics of a plant according to any of the plants described above; and optionally (e) repeating steps (c) and (d) three or more times in succession to produce selected fourth or higher backcross progeny that comprise the desired trait.

In another aspect, provided herein are methods of introducing a desired trait into a tomato variety comprising: (a) crossing a first plant of tomato variety SND-017 with a tomato plant that comprises a desired trait to produce F1 progeny; (b) selecting an F1 progeny that comprises the desired trait; (c) crossing the selected F1 progeny with a second plant of tomato variety SND-017 to produce backcross progeny; (d) selecting backcross progeny comprising the desired trait and all or essentially all the physiological and morphological characteristics of tomato variety SND-017; and optionally (e) repeating steps (c) and (d) three or more times in succession to produce selected fourth or higher backcross progeny that comprise the desired trait.

Also provided are tomato plants produced by any of the methods described above.

In another aspect, provided herein are methods of producing a plant comprising an added desired trait, the method comprising introducing a transgene conferring the desired trait into a plant of tomato variety SND-017.

In another aspect, provided herein are methods of determining a genotype of any of the plants described above, the methods comprising obtaining a sample of nucleic acids from said plant and detecting in said nucleic acids a plurality of polymorphisms. In some embodiments, the methods further comprise a step of storing the results of detecting the plurality of polymorphisms on a computer readable medium.

In another aspect, provided herein are methods for producing a seed of a variety derived from tomato variety SND-017, comprising the steps of: (a) crossing a tomato plant of variety SND-017 with a second tomato plant to form a fertilized tomato plant of variety SND-017; and (b) cultivating the fertilized tomato plant of variety SND-017 until it forms a seed. In some embodiments, the methods further comprise the steps of: (c) crossing a plant grown from the seed of step (b) with itself or a third tomato plant to form a second fertilized tomato plant of variety SND-017, (d) cultivating the second fertilized tomato plant of variety SND-017 until it forms an additional seed; (e) growing said additional seed of step (d) to yield a third tomato plant of variety SND-017; and optionally (f) repeating the crossing and growing steps of (c) and (e) to generate additional tomato plants of variety SND-017. In some embodiments, the second tomato plant is of an inbred tomato variety.

Also provided herein are plants comprising any of the scions or rootstocks described above.

In another aspect, provided herein are methods for producing a tomato fruit, the method comprising growing in a field or an area of cultivation a plant according to any of the plants described above or a seed or seedling thereof to produce a plant and cultivating the plant to produce a tomato fruit. In some embodiments, the method further comprises harvesting the tomato fruit from the plant.

In another aspect, provided herein are food or feed products comprising any of the plant parts described above.

BRIEF DESCRIPTION OF THE DRAWINGS

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

FIG. 6A shows a comparison of tomato mass for clone 17 tomatoes and control tomatoes three weeks after harvesting, FIG. 6B shows a comparison of CHG methylation between clone 17 tomatoes and control tomatoes, FIG. 6C shows overall percent methylation in the SlFSR gene and surrounding area, and FIG. 6D shows CG, CHG, and CHH methylation within 5 kb up-stream and downstream of the transcription start site.

DETAILED DESCRIPTION

Figure 1:
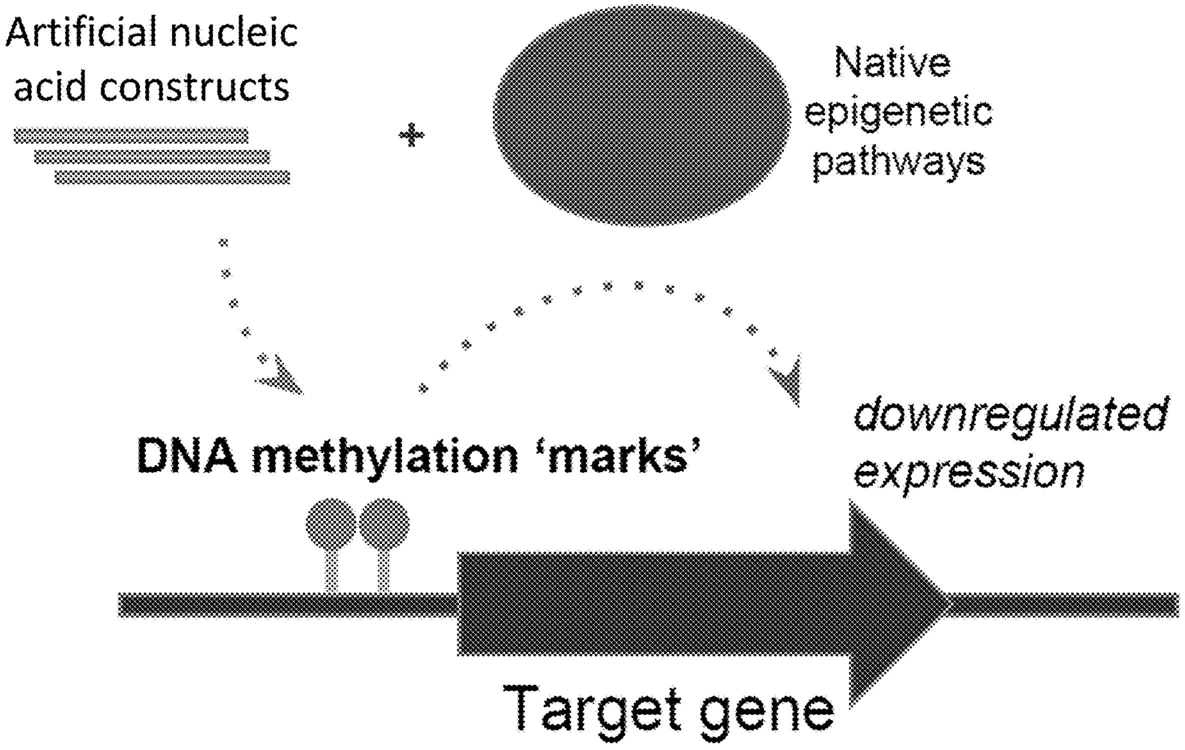
FIG. 1 is a schematic depiction of a method of reducing expression of a target gene, according to aspects of this disclosure.

The following description recites various aspects and embodiments of the present compositions and methods. No particular embodiment is intended to define the scope of the compositions and methods. Rather, the embodiments merely provide non-limiting examples of various compositions and methods that are at least included within the scope of the disclosed compositions and methods. The description is to be read from the perspective of one of ordinary skill in the art; therefore, information well known to the skilled artisan is not necessarily included.

I. Terminology

The following definitions are provided to assist the reader. Unless otherwise defined, all terms of art, notations, and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not be construed as representing a substantial difference over the definition of the term as generally understood in the art.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of" and "consisting of" those certain elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

Recitation of ranges of values-herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

The terms "about" and "approximately" as used herein-shall generally mean an acceptable degree of error for the quantity measured given the nature or precision of the measurements. Exemplary degrees of error are within 20% (%); preferably, within 10%; and more preferably, within 5% of a given value or range of values. Any reference to "about X" or "approximately X" specifically indicates at least the values X, 0.95X, 0.96X, 0.97X, 0.98X, 0.99X, 1.01X, 1.02X, 1.03X, 1.04X, and 1.05X. Thus, expressions "about X" or "approximately X" are intended to teach and provide written support for a claim limitation of, for example, "0.98X." Alternatively, in biological systems, the terms "about" and "approximately" may mean values that are within an order of magnitude, preferably within 5-fold, and more preferably within 2-fold of a given value. Numerical quantities given herein are approximate unless stated otherwise, meaning that the term "about" or "approximately" can be inferred when not expressly stated. When "about" is applied to the beginning of a numerical range, it applies to both ends of the range.

The term "plant" can be used interchangeably with the term "crop" and can include, but, is not limited to, any crop, cultivated plant, fungus, or alga that may be harvested for food, clothing, livestock fodder, biofuel, medicine, or other uses. For example, plants include field and greenhouse crops, including but not limited to broad acre crops, fruits and vegetables, perennial tree crops, and ornamentals. Plants include, but are not limited to sugarcane, pumpkin, maize (corn), wheat, rice, cassava, soybeans, hay, potatoes, cotton, tomato, alfalfa, and green algae. Plants also include, but are not limited to any vegetable, such as cabbage, turnip, carrot, parsnip, beetroot, lettuce, beans, broad beans, peas, potato, eggplant, tomato, cucumber, pumpkin, squash, onion, garlic, leek, pepper, spinach, yam, sweet potato, and cassava. In some instances, the plant can also include a plant part, e.g., a fruit, a leaf, a stalk, pollen, an ovule, a root, a flower, a plant embryo, a scion, a rootstock, a seedling, or any combination thereof.

The tomato is the edible berry of the plant *Solanum lycopersicum*, commonly known as a tomato plant. Numerous varieties of the tomato plant are widely grown in temperate climates across the world, with greenhouses allowing for the production of tomatoes throughout all seasons of the year. Tomato plants are dicots, and grow as a series of branching stems. Indeterminate tomato plants are "tender" perennials, dying annually in temperate climates, although they can live up to three years in a greenhouse in some cases. Determinate types are annual in all climates. As a true fruit, the tomato develops from the ovary of the plant after fertilization, its flesh comprising the pericarp walls. The fruit contains hollow spaces full of seeds and moisture, called locular cavities. These vary, among cultivated species (varieties), according to type. Some smaller varieties have two cavities, while globe-shaped varieties typically have three to five.

Six horticultural ripening grades for tomatoes are typically distinguished based on color schemes: mature green, breaker, turning, pink, light red, and red. At the green stage, the surface of the tomato is completely green in color, though the shade may vary. Once a tomato starts changing its color from the mature green stage to some other color (e.g., tannish-yellow, pink, or red), it is at the breaker stage. Usually the other color is not more than 10% of the surface. At the turning stage, more than 10% but not more than 30% of the surface, in aggregate, shows a definite change from green to another color (tannish-yellow, pink, red, or a combination thereof). At the pink stage, more than 30% but not more than 60% of the surface, in aggregate, show pink or red in color. At the light red stage, more than 60% of the surface, in aggregate, shows pinkish-red or red coloring but not more than 90% of the surface is red. The red stage means that more than 90% of the surface, in aggregate, is red.

As used throughout, the term "nucleic acid" or "nucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar properties as the reference nucleic acid and are metabolized in a manner similar to naturally occurring nucleotides. A nucleic acid sequence can comprise combinations of deoxyribonucleic acids and ribonucleic acids. Such deoxyribonucleic acids and ribonucleic acids include both naturally occurring molecules and synthetic analogues. The polynucleotides of the invention also encompass all forms of sequences including, but not limited to, single-stranded forms, double-stranded forms, hairpins, stem-and-loop structures, and the like.

Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)).

The terms "identity," "homologous," "homology," or "percent homology" as used herein refer to the degree of sequence similarity between an amino acid or nucleotide sequence and a reference sequence. As used herein, the term "homology" can be used interchangeably with the term "identity." In some instances, the degree of sequence similarity herein can be at least about 60%, at least about 65%, at least about 70%, at least about 75%, at least about 80%, at least about 85%, at least about 90%, or at least about 95%, or about 100%. In some instances, percent sequence homology can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). Percent homology of sequences can be determined using the most recent version of BLAST, as of the filing date of this application. In some instances, percent homology of sequences can be determined using Smith-Waterman homology search algorithm. Smith & Waterman (1981) Adv. Appl. Math. 2: 482-489.

Percent homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues. Most sequence comparison method over longer sequences are designed to produce optimal alignments that take into consideration possible insertions and deletions without penalizing unduly the overall homology score. This is achieved by inserting "gaps" in the sequence alignment to try to maximize local homology. These more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is a commonly used gap scoring system. High gap penalties will of course produce optimized alignments with fewer gaps. Most alignment programs allow the gap penalties to be modified. Typically the default values are used when using such software for sequence comparisons. Calculation of maximum % homology therefore firstly requires the production of an optimal alignment, taking into consideration gap penalties. Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. In some instances, an alignment is determined by the Smith-Waterman homology search algorithm using an affine gap search with a gap open penalty of 12 a gap extension penalty of 2, and a blocks substitution matrix (BLOSUM) of 62.

The term "transcription regulatory region" refers to any genomic region or nucleotide sequence that is able to regulate transcription of a particular gene in a cell or organism of interest. Transcription regulatory regions include, but are not limited to, promoters, translational termination regions, transcriptional initiation start sites, operators, activators, enhancers, other regulatory elements, ribosomal binding sites, an initiation codon, termination signals, and the like. A transcription regulatory region for a particular gene may be within the gene body (i.e., the entire sequence of the gene from the transcription start site to the transcription termination site), upstream or downstream of the gene body (i.e., proximal to the gene), or located further away on the same chromosome as the gene or on a different chromosome from the gene (i.e., distal to the gene). Transcription regulatory regions may be endogenous or heterologous to the host cell or to each other. As used herein, "heterologous" in reference to a sequence is a sequence that originates from a foreign species, or, if from the same species, is substantially modified from its native form in composition and/or genomic locus by deliberate human intervention. See Sambrook et al. (1992) Molecular Cloning: A Laboratory Manual, ed. Maniatis et al. (Cold Spring Harbor Laboratory Press, Cold Spring Harbor, N.Y.); Davis et al., eds. (1980) Advanced Bacterial Genetics (Cold Spring Harbor Laboratory Press), Cold Spring Harbor, N.Y., and the references cited therein.

II. Introduction

Provided herein are modified tomato plants comprising an introduced modification at the SlFSR gene or a transcription regulatory region thereof. In some embodiments, the introduced modification is an epigenetic modification. In some embodiments, the introduced epigenetic modification comprises hypermethylation of genomic DNA at the SlFSR gene or a transcription regulatory region thereof. In some embodiments, the introduced modification is heritable. Also provided are progeny plants produced from the modified tomato plants, tomato seeds and tomato fruit produced by the modified tomato plants or progeny plants, and associated methods and nucleic acid reagents. In some embodiments, the tomato fruits described herein display extended shelf life relative to tomato fruit produced from unmodified tomato plants.

The tomato gene SlFSR is a member of the GRAS protein family, a recently identified plant-specific family of putative transcription factors. The SlFSR gene is located on chromosome 7 at nucleotide positions 61,367,195 to 61,368,484 in the SL2.5 *Solanum lycopersicum* reference genome available at solgenomics.net. The gene sequence is listed under Solanaceae Genomic Network accession no. Solyc07g052960 (SEQ ID NO:83). In the sequenced genome of the Brandywine tomato variety (available at solgenomics.net/projects/tomato13/), the translation start site of SlFSR is at nucleotide position 61515621 on chromosome 7. In the Heinz tomato reference genome (available at solgenomics.net/organism/*Solanum lycopersicum*/genome/), the translation start site of SlFSR is at nucleotide position 61290360 on chromosome 7. The GRAS family proteins play various critical roles in growth and development, such as in root development, phytohormones, light signaling pathways, and transcriptional regulation in response to biotic and abiotic stress. encodes a protein product that contributes to regulation of cell wall biosynthesis. Recent studies have shown that reduced expression of the gene in tomato plants can lead to increased shelf life of tomato fruit produced from the plants (Zhang et al., 2018, J. Exp. Bot. 69(12):2897-2909), suggesting that SlFSR plays an essential role in fruit post-harvest storage.

In some embodiments of the modified tomato plants, and progeny, fruits, and seeds thereof, and associated methods provided herein, the modifications are made using molecular techniques for reducing expression of specific target genes in plants to elicit the desired phenotype of commercial value. In some embodiments, useful molecular techniques for this purpose are described in PCT Appl. No. WO2020191072A1, which is hereby incorporated by reference in its entirety. In some instances, this technology uses specifically engineered DNA oligonucleotide constructs (i.e. artificial nucleic acid constructs) to induce nitrogenous base modification (e.g., cytosine methylation) and epigenetic silencing of target genes (i.e. full or partial decrease in expression from the genes without modification of the DNA sequences of the genes). Such artificial nucleic acid constructs can be designed with high sequence homology to a transcription regulatory region upstream of the open reading frame of a target gene. In some embodiments, the transcription regulatory region is endogenous or heterologous to the host cell or organism. In some instances, the artificial nucleic acid constructs can be double stranded DNA constructs having at least one end overhang, such that the DNA construct mimics the double stranded RNA recognized by the plant's endogenous DNA methylation machinery, thereby directing endogenous DNA methylation to the transcription regulatory region. An exemplary embodiment of the molecular techniques described above is shown in FIG. 1. In some instances, methylation of cytosines in a gene or transcription regulatory region of a gene leads to a reduction in expression of the gene. In some embodiments, the modified bases (e.g., methylated cytosines) are heritable, enabling generation of parental breeding lines with desired expression profiles. Thus, methylation and altered transcript levels can be propagated through future progeny generations. Heritability of DNA methylation in plants is discussed, for example, in Ashapkin et al., 2016, Russian J. Plant Phys. 63:181-192.

III. Modified Tomato Plants

In one aspect, provided herein are modified tomato plants and products thereof (e.g., fruit, seeds, offspring plants) comprising an introduced modification of genomic DNA at the SlFSR gene or a transcription regulatory region thereof. As used herein an "introduced modification" is a modification made to the physical structure of the genomic DNA by a molecular biology technique that does not alter the primary sequence of the DNA and that is not present in an unmodified (i.e. control) plant. An introduced modification is made by human activity. In some embodiments, the introduced modification is heritable. In some embodiments, the introduced modification can be passed from the modified tomato plant to its offspring and from its offspring to subsequent generations of offspring. In some embodiments, the introduced modification reduces expression of the SlFSR gene in the modified tomato plant. As used herein, "reduced expression" or grammatical variations thereof refers to a decrease in production of a gene product (e.g., an mRNA transcript, a noncoding RNA, or a protein). In some embodiments, the introduced modification is an epigenetic modification. In some instances, the introduced modification comprises at least one methylated base in a transcription regulatory region (e.g., upstream of the gene, within the gene body, downstream of the gene, or a distal enhancer region) of the SlFSR gene. In some instances, the introduced modification comprises a plurality of methylated bases in a transcription regulatory region of the SlFSR gene. In some embodiments, the introduced modification is not a transgene. In some instances, the transcription regulatory region comprises at least one selected from the group consisting of: a transcription start site, a TATA box, and an upstream activating sequence. In some instances, the methylated base(s) in the modified tomato plant are not typically methylated in the genome of an unmodified tomato plant.

In some embodiments, the modified tomato plants of this disclosure include a particular modified tomato plant. Such modified tomato plants include tomato variety SND-017, a Brandywine plant variety created using the methods provided herein, as described in the Examples of this disclosure, that produces modified tomato fruit that has an extended shelf life relative to a tomato fruit produced from an unmodified Brandywine variety plant. In some embodiments, SND-017 is marketed as tomato variety SUMMER SWELL.

Also provided herein are plant parts of any of the modified plants described herein. In some embodiments, the plant part comprises a leaf, pollen, an ovule, a fruit, a scion, a rootstock, or a cell.

In some embodiments, the introduced epigenetic modification comprises hypermethylation of genomic DNA at the SlFSR gene or a transcription regulatory region thereof. As used herein, "hypermethylation" refers to a level of methylation (e.g., DNA methylation) at a genomic region (e.g., a locus) that is increased in an individual relative to the level of methylation in that same genomic region in a control untreated plant. For example, a modified tomato plant having hypermethylation of DNA at the SlFSR gene may have an increased level of DNA methylation at the SlFSR gene relative to the level of DNA methylation at this region in other unmodified tomato plants. In some embodiments, the modified tomato plants provided herein comprise hypermethylation of genomic DNA at the SlFSR gene or a transcription regulatory region thereof. In some embodiments, the hypermethylation is within a 1 kilobase (kB) region upstream of the translation start site of SlFSR. In some embodiments, the hypermethylation is within a 0.5 kB region upstream of the translation start site of SlFSR. Methods of detecting DNA methylation are known in the art, and include the methods described herein below.

An epigenetic modification may occur at any base in a nucleic acid sequence of a genome, such as a cytosine, a thymine, a uracil, an adenine, a guanine, or any combination thereof. The epigenetic modification may be a heritable epigenetic modification, such as an epigenetic modification passed to at least one progeny of an organism. The epigenetic modification may be an engineered epigenetic modification, such as an epigenetic modification that is not non-naturally occurring at a particular base in a nucleic acid sequence of a native organism but one that is introduced into the organism or into an ancestor of an organism using a method as described herein. An organism may comprise a heritable epigenetic modification that may have been previously introduced into a parent organism or an ancestor organism that is retained for at least one reproduction cycle.

In some embodiments, the modified tomato plant have a reduced expression level of a gene product encoded by the SlFSR gene. In some embodiments, the gene product is an mRNA transcript encoded by the SlFSR gene. In some embodiments, the gene product is a protein encoded by the SlFSR gene. In some embodiments, the expression level of the gene product is reduced relative to the expression level of the gene product encoded by the SlFSR gene in an unmodified tomato plant. As used herein, an "unmodified tomato plant" refers to a plant of the same variety as the modified tomato plant but that does not comprise the introduced epigenetic modification of genomic DNA at the SlFSR gene or a transcription regulatory region thereof. In some instances, the unmodified tomato plant is grown from seeds that are untreated or are control-treated. For example, as described in the Examples, control-treated plants are grown from control-treated seeds that are treated with a formulation that does not cause the introduced epigenetic modification of genomic DNA at the SlFSR gene or a transcription regulatory region thereof (e.g., does not contain the artificial nucleic acid constructs described below). Unless stated otherwise, modified tomato plants (or products thereof) are compared to unmodified tomato plants that are of the same variety and are grown in a similar manner under similar conditions. In some embodiments, gene product expression levels in a modified plant are reduced by at least about 5% (e.g., at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or at least about 100%) relative to gene produce expression levels in an unmodified plant. Methods for detecting a reduction in gene product expression levels are known in the art and include, but are not limited to, RNA sequencing, quantitative polymerase chain reaction, Northern blots, microscopy (e.g., fluorescence microscopy), fluorescence in situ hybridization (FISH, e.g., RNA FISH), immunohistochemistry, Western blots, and mass spectrometry.

In some embodiments of the modified tomato plants and products thereof described herein, the tomato modified plants comprise a wild type SlFSR gene (i.e., the gene coding sequence is identical to the nucleic acid sequence of SEQ ID NO:83). In some embodiments, the modified tomato plants comprise an SlFSR gene with one or more mutations. In some embodiments, the one or more mutations impair or abolish the function of SlFSR. In some embodiments, the one or more mutations contribute to a desired phenotype in the modified tomato plant (e.g., production of tomato fruit with increased shelf life, as described herein below). In some embodiments, the modified tomato plants comprise one or more mutations in one or more other genes. In some embodiments, the one or more mutations in one or more other genes contribute to a desired phenotype in the modified tomato plant (e.g., production of tomato fruit with increased shelf life, as described herein below). In some embodiments, the modified tomato plants comprise one or more transgenes and/or other modifications to the genome sequence. In some embodiments, the one or more transgenes and/or other modifications contribute to a desired phenotype to the modified tomato plant (e.g., production of tomato fruit with increased shelf life, as described herein below).

In some embodiments, the modified tomatoes of the present disclosure may be derived from any tomato variety. In some embodiments, the modified tomato plant is of any currently known or unknown variety. As used herein, a "variety" is a defined group of plants within a plant species having a common set of characteristics and may include cultivated plant groups (i.e., cultivated varieties or "cultivars") or wild plant groups. In some embodiments, the tomato variety is selected from a variety listed in the New Jersey Agricultural Experiment Station Tomato Varieties database (available at njaes.rutgers.edu/tomato-varieties/). Heirloom tomato varieties are open-pollinated, non-hybrid tomato plant varieties. "Open-pollinated" refers to seeds that produce offspring with similar traits, regardless of whether they are self-pollinated or are pollinated by another representative of the same variety. In contrast, hybrid plants may show a wide array of different characteristics between generations, due to the mixture of genetic information. In some embodiments, the modified tomato plant is of a commercially available variety. In some embodiments, the modified tomato plant is of a hybrid variety. Tomato varieties include, but are not limited to, Ailsa Craig, Anna Russian, Applause, Aussie, Baladre, Beefsteak, Bella rosa, Better Boy, Big Beef, Black cherry, Black russian, Blondkopfchen, Brandywine, Coal, Ceylan, Cherokee purple, Cherry, Cherry Roma, Round Cherry, Yellow Pear Cherry Tomato, Comanche, Costoluto Genovese, Ditmarcher, Eros, Gallician, Glacier, Gartenperle, Green Sausage, Grushovka, Harzfeuer, Hugh, Japanesse Black, Jersey Devil, Kosovo, Krim Black, Kumato, Liguria, Limachino, Lime Green Salad, Manitoba, Marvel Stripe, Matina, Micro Tom, Moneymaker, Muxamiel, Estrella, Opalka, RAF, Black Pear, Hawaiian Pineapple, Rio Grande, San Marzano, Siberian, Sprite, Sugary, Sun sugar, Tigerella, White Queen, Raf Claudia, Rome, Valencian, Pear of Girona, Montserrat, Ox Heart Angela, Hang on Branch, Black Plum, Optima, Black Paw, Copy, Velasco, Montenegro, Vertyco, Ventero, Ramyle, Pitenza, Paladium, Mayoral, Razymo, Motto, Caniles, Byelsa, Royalty, Trujillo, Delizia, Dumas Duratom, Stringer, Torry, Tovistar, Painter, Thick, Long Life, Marenza, Window box Roma, Ninette, Retinto, Boludo, Anairis, Tobi Star, Myla, Guarapo, Atago, Jawara, Velasco, Manitu, Colbi, Duraton, Patriarch, Danube, Intense, Pear Fitto, Vernal, Cecilio, Cherry Kumato, Cherry Yellow, Round Cherry, Cherry Ministar, Cherry Sour Cherries, Cherry Marinica and Cherry Angel. In some embodiments, the modified tomato plant is of an heirloom variety. In some embodiments, the modified tomato plant is of a Brandywine variety. In some embodiments, the modified tomato plant is of a Micro Tom variety. In some instances, heirloom tomatoes can have a shorter shelf life and/or can be less disease resistant than hybrid varieties, but can have flavor profiles favored by consumers. In some embodiments, the modified tomato plants provided herein produce tomato fruit with extended shelf life and are of an heirloom variety. By providing heirloom tomato fruits with extended shelf life, the present disclosure solves an important commercial need.

Also provided herein are modified tomato plants that are offspring of any of the modified tomato plant described above. In some instances, such an offspring is grown from a seed of the modified tomato plant. In some embodiments, the offspring tomato plants are substantially similar to the parent modified tomato-plant. In some embodiments, the offspring tomato plant comprises the epigenetic modification comprising hypermethylation of genomic DNA at the SlFSR gene or a transcription regulatory region thereof (e.g., within a 1 kB region or a 0.5 kB region upstream of the translation start site of SlFSR). In some embodiments, the offspring tomato plant has a reduced level of a gene product (e.g., an mRNA transcript or a protein) encoded by the SlFSR gene.

In some instances, the introduced modification of the modified tomato plant is heritable. In some embodiments, the introduced modification can be passed from the modified tomato plant to its offspring and from its offspring to subsequent generations of offspring. In some instances, the introduced heritable modification is detectable for at least about: 2, 3, 4, 5, 6, 7, 8, 9, 10, 15, 20, or 30 reproduction cycles. In some instances, offspring tomato plants produced from the modified tomato plants comprise the heritable introduced modification for at least about: 2, 3, 4, 5, 6, 7, 8, 9, 10, 15, 20, or 30 generations. In some instances, offspring tomato plants produced from the modified tomato plants comprise hypermethylation at the SlFSR gene or a transcription regulatory region thereof for at least about: 2, 3, 4, 5, 6, 7, 8, 9, 10, 15, 20, or 30 generations. In some instances, expression of SlFSR is reduced for at least about: 2, 3, 4, 5, 6, 7, 8, 9, 10, 15, 20, or 30 reproduction cycles. In some instances, offspring tomato plants produced from the modified tomato plants have reduced expression of SlFSR for at least about: 2, 3, 4, 5, 6, 7, 8, 9, 10, 15, 20, or 30 generations.

In some embodiments, the modified tomato plants comprise additional modifications and/or characteristics (e.g., transgenes, genome edits, growth conditions) that confer a desirable phenotype (e.g., extended tomato fruit shelf life). One such modification is described in Nambeesan et al., 2010, Plant J. 63(5):836-847.

Also provided herein are modified tomato fruits produced by any of the modified tomato plants described above. In some embodiments, the modified tomato fruit has an extended shelf life relative to a tomato produced from an unmodified tomato plant. In some embodiments, the modified tomato fruit has a shelf life that is increased relative to a tomato produced from an unmodified tomato plant by at least about 5% (e.g., at least about 10%, at least about 15%, at least about 20%, at least about 25%, at least about 30%, at least about 40%, at least about 50%, at least about 60%, at least about 70%, at least about 80%, at least about 90%, at least about 95%, at least about 99%, at least about 100%, or more). In some embodiments, the modified tomato fruit has a shelf life that is increased relative to a tomato produced from an unmodified tomato plant by at least about 1.5, 2, 3, 4, 5, 6, 7, 8, 9, 10, 11, 12, 13, 14, 15, 16, 17, 18, 19, 20, 25, 30, 40, 50-fold or more.

Figure 2:
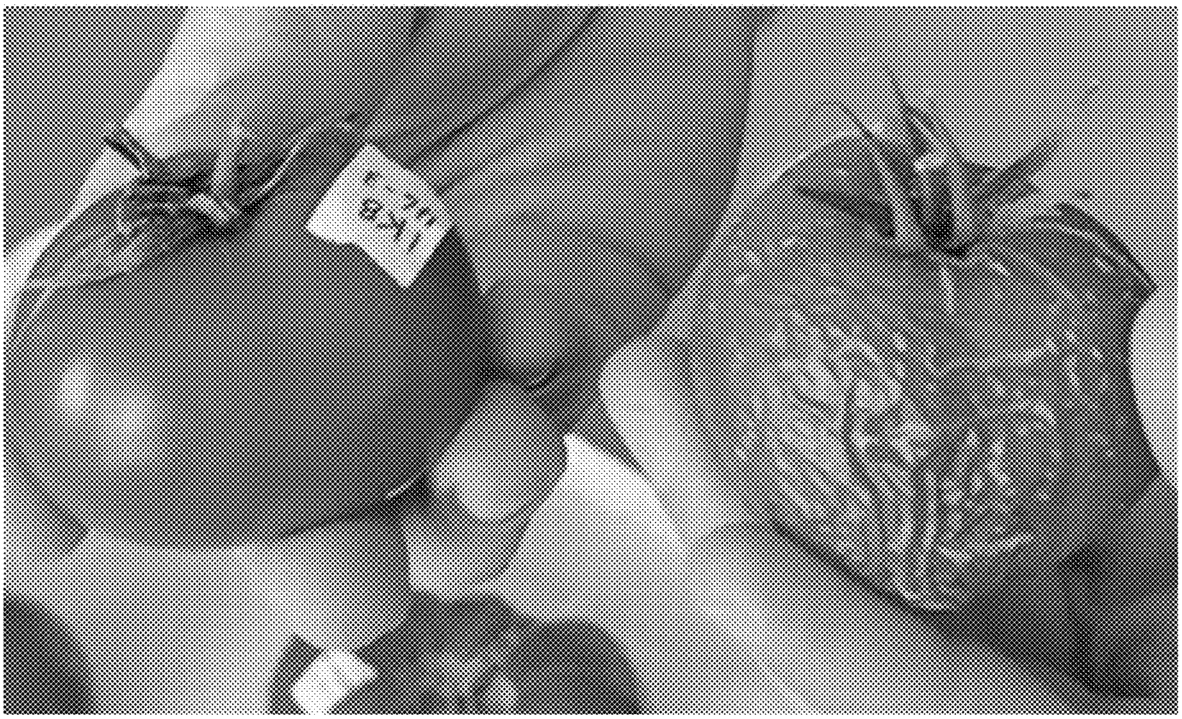
FIG. 2 is a photograph of representative tomato fruits from a modified tomato plant (left side) and an unmodified tomato plant (right side), according to aspects of this disclosure. Both tomato fruits are shown at 12 days post-harvest.

Any suitable method may be used to measure tomato fruit shelf life. In some embodiments, tomato fruit shelf life is measured by visual inspection (e.g., skin smoothness/wrinkles, cracking). For example, FIG. 2 shows a tomato produced from a modified tomato plant on the left (smooth skin, no cracking) and a tomato fruit produced from an unmodified tomato plant on the right (wrinkled skin, cracking), indicating that the tomato fruit on the left has a longer shelf life. In some embodiments, tomato fruit shelf life is measured by monitoring water loss over time (e.g., via monitoring tomato fruit weight), with fruits having a longer duration of shelf life also having slower rates of water loss, or. See, e.g., the methods described in Zhang et al., 2018, J. Exp. Bot. 69(12):2897-2909. In some embodiments, tomato fruit shelf life is measured by assessing fruit firmness. For example, fruit firmness can be assessed using a non-destructive penetrometer as described in the Examples herein. One suitable non-destructive penetrometer is the HPE III Fff testing device available from Bareiss. Using this device, a high reading (e.g., of hard fruit at or before harvest) would generally score in the 60-80 range, while low readings are generally in the 10-15 range. Typically, tomato fruits lose firmness over time, eventually becoming too soft to assay further. This point can be used as an assay end point. With the HPE III Fff device, this point is generally around a value of 10. One of skill in the art will appreciate that various devices may be used, and that the relative measurement values may need to be determined separately for each device. In some embodiments, tomato fruit shelf life is measured by monitoring tomato fruit mass over time. In some embodiments, tomato fruit firmness (e.g., as measured using a penetrometer) and/or tomato fruit mass and/or tomato fruit appearance can be measured at harvest and at various time points after harvest (e.g., every day, every 2 days, every 3 days, every 4 days, every 5 days, every 6 days, or every 7 days). Comparison of the values at harvest to those at the post-harvest time points can give a percentage measurement of decrease in mass and/or decrease in firmness. For example, a tomato that has a mass of 200 grams at harvest and a mass of 150 g at 7 days after harvest has shown a 25% decrease in mass.

In some embodiments, the modified tomato fruits provided herein retain at least a pre-determined minimum degree of firmness of for at least 1 day (e.g., at least 2 days, at least 4 days, at least 7 days, at least 10 days, at least 14 days, at least 18 days, at least 21 days, at least 25 days, at least 28 days, or at least 31 days) after harvesting. In some embodiments, the modified tomato fruits provided herein retain a firmness of at least 10 as measured on a Bareiss HPE III Fff device for at least 1 day (e.g., at least 2 days, at least 4 days, at least 7 days, at least 10 days, at least 14 days, at least 18 days, at least 21 days, at least 25 days, at least 28 days, or at least 31 days) after harvesting. In some embodiments, the modified tomato fruits provided herein retain a firmness of at least 15 as measured on a Bareiss HPE III Fff device for at least 1 day after harvesting. In some embodiments, the modified tomato fruits provided herein retain an increased degree of firmness relative to an unmodified tomato fruit (e.g., of the same variety) harvested at the same time for at least 1 day after harvesting. In some embodiments, the modified tomato fruits provided herein retain at least a pre-determined minimum degree of for at least 1.3 times as long as an unmodified tomato fruit (e.g., at least 1.3X, 1,4X, 1.5X, 1.6X, 1.7X, 1.8X, 1.9X, 2.0X, 2.2X, 2.5X, 2.8X, or 3.0X). In some embodiments, the modified tomato fruits provided herein have increased water content relative to an unmodified tomato fruit harvested at the same time for at least 1 day (e.g., at least 2 days, at least 4 days, at least 7 days, at least 10 days, at least 14 days, at least 18 days, at least 21 days, at least 25 days, at least 28 days, or at least 31 days) after harvesting.

In some embodiments, the modified tomato fruits provided herein may be treated, stored, or processed in various ways to further prolong shelf life. In some embodiments, the modified tomato fruit is treated with a coating to reduce ethylene release (e.g., an ethylene absorbing film or coating) or storage in packaging that reduces ethylene release or absorbs ethylene. In some embodiments, the modified tomato fruit is stored in conditions promoting increased shelf life, e.g., in a climate-controlled environment. In some embodiments, the modified tomato fruit is stored (e.g., in a climate-controlled environment) at a temperature between 8° C. and 24° C. (e.g., 8° C., 9° C., 10° C., 11° C., 12° C., 13° C., 14° C., 15° C., 16° C., 17° C., 18° C., 19° C., 20° C., 21° C., 22° C., 23° C., or 25° C. For example, the modified tomato fruit can be stored at a temperature of 8-12° C., 10-14° C., 12-16° C., 10-15° C., 15-20° C., 18-24° C., 20-24° C., or 18-22° C. In some embodiments, the modified tomato fruits are treated with a post-harvest treatment such as, for example, those described in Mahajan et al., 2014, Philos. Trans. A. Math Phys. Eng. Sci. 372(2017):20130309.

Also provided herein are modified tomato seeds produced by any of the modified tomato plants described herein or contained in any of the modified tomato fruits described herein. In some embodiments, the seed is of tomato plant variety SND-017. In some embodiments, the modified tomato seeds are treated to promote extended shelf life in tomato fruits produced by tomato plants grown from the modified tomato seeds. Also provided are plants produced by growing the seeds provided herein, as well as plant parts thereof. In some embodiments, the plant parts comprise a leaf, pollen, an ovule, a fruit, a scion, a rootstock, and/or a cell. Also provided are tomato plants, and parts thereof, having all or essentially all of the physiological and morphological characteristics of any of the tomato plants described herein.

Also provided herein are isolated or cultured cells of any of the modified tomato plants, modified tomato fruits, and/or modified tomato seeds described herein. In some embodiments, the isolated or cultured cells are from an embryo, a meristem, a cotyledon, a pollen, a leaf, an anther, a root, a root tip, a pistil, a flower, a seed, and/or a stalk. In some embodiments, the isolated or cultured cells comprise protoplasts. In some embodiments, the isolated or cultured cells are regenerable (i.e., are able to give rise to plants under suitable conditions). Also provided are populations of cells comprising a plurality of the isolated or cultured cells. Also provided are tomato plants regenerated from the isolated or cultured cells.

Also provided herein are foods or feed products comprising a plant part of any of the modified tomato plants described herein. In some embodiments, the foods or feed products comprise modified tomato fruits as described herein.

IV. Methods and Associated Nucleic Acid Compositions

In another aspect, provided herein are methods associated with the modified tomato plants (and products thereof) described above. In some embodiments, provided herein are methods for growing the modified tomato plants and methods for producing the modified tomato fruits and the modified tomato plants. Also provided are compositions and nucleic acids useful in the methods described herein.

A. Growing Modified Plants and Producing Modified Fruits

In one aspect, provided herein are methods for growing any of the modified tomato plants described herein. In some embodiments, the methods comprise growing in a field or an area of cultivation a modified tomato plant described herein or a seed or seedling thereof. It will be appreciated by one of skill in the art that suitable growing conditions can be selected and/or optimized based on the particular characteristics of the modified tomato plant being grown, as well as the desired traits in the growing modified tomato plant, the mature modified tomato plant, and/or the products produced from the modified tomato plant (e.g., seeds, offspring plants, tomato fruits). Fields useful in the methods herein may comprise any arable land suitable for growing tomato plants. In some embodiments, a field in a location with a climate suitable for the growth of tomato plants is used in the methods herein. Areas of cultivation may include indoor growing areas (e.g., greenhouses, growth chambers) or hydroponic mechanisms. Additional growth conditions (e.g., planting season, soil treatment, growth temperature, humidity, watering scheme, fertilizer usage, harvest timing, etc.) may be selected by one of skill in the art to optimize desired characteristics.

Also provided are methods for producing a modified tomato fruit. In some embodiments, the methods comprise growing a field or an area of cultivation any of the modified tomato plants described herein or a seed or seedling thereof to produce a modified tomato plant and cultivating the modified tomato plant (e.g., as described above) to produce a modified tomato fruit. In some embodiments, the methods comprise harvesting the modified tomato fruit from the modified tomato plant.

Also provided are methods for vegetatively propagating any of the modified tomato plants described herein. In some embodiments, the methods comprise collecting tissue capable of being propagated from the plant. In some embodiments, the methods comprise cultivating said tissue to obtain proliferated shoots. In some embodiments, the methods comprise rooting said proliferative shoots to obtain rooted plantlets. In some embodiments, the methods comprise growing plants from said rooted plantlets.

B. Methods of Producing Modified Tomato Plants

Also provided herein are methods of producing the modified tomato plants described herein. In some embodiments, the methods described herein produce a modified tomato plant having reduced expression of a gene (e.g., the SlFSR gene) in the modified tomato plant or any constituent part thereof, including a modified tomato fruit or seed produced by the tomato plant. In some embodiments, the methods produce modified tomato plants comprising an introduced modification comprising hypermethylation of genomic DNA at the SlFSR gene or a transcription regulatory region thereof. In some embodiments, the introduced modification is a heritable modification that can be passed from the modified tomato plant to its offspring and from its offspring to subsequent generations of offspring. The methods can comprise contacting a tomato plant, a tomato seed, a constituent of a tomato plant (e.g., a leaf or root), or any combinations thereof with the artificial nucleic acid constructs disclosed herein, e.g., contacting the seed with a solution of artificial nucleic acid constructs, or directly administering the artificial nucleic acid constructs to the plant. The artificial nucleic acid constructs, plants, seeds, and formulations disclosed herein may be used in agriculture. The artificial nucleic acid constructs, plants, seeds, and formulations may be used to promote extended fruit shelf life. The artificial nucleic acid constructs and formulations are described in more detail in the "Artificial nucleic acid constructs" section below.

In some embodiments, a method for producing the modified tomato plants comprises applying a formulation comprising at least one artificial nucleic acid construct to a tomato plant, a constituent of a tomato plant, or any combination thereof. In some embodiments, the formulation is a solution. In some embodiments, the formulation is a powder, granule, pellet, bead, or liquid. In some embodiments, the formulation is a liquid. In some embodiments, the liquid comprises water. In some embodiments, the formulation is a solid that is dissolvable in a liquid. Useful formulations comprising at least one artificial nucleic acid construct provided herein are described below in Section C. Artificial nucleic acid constructs.

Artificial nucleic acid constructs and formulations as described herein can be applied to a tomato plant and/or constituent part thereof in various ways. In some embodiments, artificial nucleic acid constructs or formulations are applied as a spray. For example, in some embodiments, nucleic acid constructs or formulations can be applied as a foliar spray. In some embodiments, artificial nucleic acid constructs or formulations can be injected into the plant and/or constituent part thereof. In some embodiments, artificial nucleic acid constructs or formulations can be added to the irrigation water of the plant and/or constituent part thereof or to a plant growth material that is added thereto. In some embodiments, artificial nucleic acid constructs or formulations can be applied to the habitat of the plant and/or constituent part thereof (i.e. the immediate environment surrounding the plant). In some embodiments, artificial nucleic acid constructs or formulations can be added to a plant container (e.g., pot or planter) and the plant and/or constituent part thereof placed in the plant container. In some embodiments, artificial nucleic acid constructs or formulations can be added to soil (e.g., as a soil drench) in which the plant and/or constituent part thereof is planted (placed). In some embodiments, nucleic acid constructs or formulations can be applied to the plant and/or constituent part, the immediate environment thereof, or water or other components added thereto as a powder, granule, pellet, bead, or liquid.

In some embodiments, artificial nucleic acids or formulations are applied to a tomato seed. In some embodiments, they can be applied as a seed coating or dressing. In some embodiments, they can be applied as a seed treatment. In some embodiments, a tomato seed can be placed in a solution or contacted with a formulation comprising at least one artificial nucleic acid construct (e.g., a solution comprising at least one artificial nucleic acid constructs in water). In some embodiments, the tomato seed is fully submerged in the solution or formulation. In some embodiments, the tomato seed is partially submerged in the solution or formulation. In some embodiments, the tomato seed is kept in contact with an absorbent substrate comprising the solution or formulation. In some embodiments, the tomato seed is are allowed to germinate while in contact with the solution or formulation. In some embodiments, the nucleic acid constructs or formulations can be applied to the seed as a spray. In some embodiments, nucleic acid constructs or formulations can be applied to the seed as a powder, granule, pellet, bead, or liquid. In some embodiments, the nucleic acid constructs or formulations can be injected into the seed.

In some embodiments, the artificial nucleic acid constructs provided herein are able to penetrate the tomato seed, the tomato plant, the constituent of a tomato plant, or any combination thereof. In some embodiments, the artificial nucleic acid constructs specifically hybridize to genomic DNA of the tomato seed, the tomato plant, the constituent of a tomato plant, or any combination thereof. In some embodiments, the artificial nucleic acid constructs specifically hybridize to genomic DNA loci comprising the SlFSR gene and/or a transcription regulatory region thereof. In some embodiments, the method further comprises cultivating the tomato seed, the tomato plant, the constituent of a tomato plant, or any combination thereof with a formulation comprising at least one artificial nucleic acid construct as described herein applied thereto for a period of time sufficient to produce hypermethylation of the genomic DNA of the SlFSR gene or a transcription regulatory region thereof.

In some embodiments, the method comprises applying a formulation comprising at least one artificial nucleic acid construct described herein to a tomato seed. In some embodiments, the tomato seed is produced from a modified tomato plant described herein. In other words, a seed produced from a modified tomato plant (e.g., a modified tomato plant produced by the methods described herein) may be treated according to the methods described herein. Such "re-treatment" may maintain or increase hypermethylation of genomic DNA at the SlFSR gene or a transcription regulatory region thereof.

Also provided are methods for introducing a desired trait into a tomato variety. In some embodiments, the methods comprise crossing a first plant comprising any of the modified tomato plants described herein (e.g., SND-017 plants) with a tomato plant that comprises a desired trait to produce F1 progeny. In some embodiments, the methods comprise selecting an F1 progeny that comprises the desired trait. In some embodiments, the methods comprise crossing the selected F1 progeny with a second plant comprising any of the modified tomato plants described herein to produce backcross progeny. In some embodiments, the first plant and the second plant are of the same variety. In some embodiments, the first plant and the second plant are the same plant. In some embodiments, the first plant and the second plant are different plants. In some embodiments, the methods comprise selecting backcross progeny comprising the desired trait and all or essentially all the physiological and morphological characteristics of any of the modified tomato plants described herein. In some embodiments, the methods comprise performing additional backcrosses as described herein. In some embodiments, three or more backcrosses are performed in succession to produce selected fourth or higher backcross progeny that comprise the desired trait.

Also provided are methods for producing a modified tomato seed derived from any of the modified tomato plants described herein (e.g., SND-017 tomato plants). In some embodiments, the methods comprise crossing a modified tomato plant described herein with a second tomato plant to form a fertilized modified tomato plant. In some embodiments, the methods comprise cultivating the fertilized modified tomato plant until it forms a modified tomato seed. In some embodiments, the methods further comprise crossing a plant grown from the modified tomato seed with itself or a third tomato plant to form a second fertilized modified tomato plant. In some embodiments, the methods comprise cultivating the second fertilized modified tomato plant until it forms an additional modified tomato seed. In some embodiments, the methods comprise growing the additional modified tomato seed to yield a third modified tomato plant. In some embodiments, the steps described above are repeated to generate additional modified tomato plants (and modified tomato seeds thereof). In some embodiments, the second tomato plant and the third tomato plant are the same plant (or of the same plant variety). In some embodiments, the second tomato plant and the third tomato plant are different plants. In some embodiments, the second tomato plant and/or the third tomato plant are of an inbred tomato variety.

In some embodiments, provided herein are methods for producing a modified tomato plant comprising an added desired trait. In some embodiments, the methods comprise introducing a transgene conferring the desired trait into any of the modified tomato plants described herein (e.g., SND-017 tomato plants). In some embodiments, the methods comprise introducing the added desired trait by gene editing the genome of any of the modified tomato plants described herein (e.g., SND-017 tomato plants) to introduce the added desired trait into the modified tomato plant. Methods of performing these methods are well-known and routine in the art.

Also provided are tomato plants produced by any of the methods described herein, as well as plant parts thereof.

C. Artificial Nucleic Acid Constructs

Also provided herein are artificial nucleic acid constructs useful for inducing hypermethylation at the SlFSR gene or a transcription regulatory region thereof, wherein the nucleic acid construct is configured to guide endogenous modification (e.g., methylation) of at least one base of the SlFSR gene or a transcription regulatory region thereof in the organism. In some instances, the artificial nucleic acid construct comprises a double stranded oligonucleotide comprising (a) a first strand having a length of 10 to 100 nucleotides or nucleosides or a combination thereof and comprising at least 60% identity (e.g., at least 65%, 70%, 75%, 80%, 85%, 90%, 91%, 92%, 93%, 94%, 95%, 96%, 97%, 98%, 99%, or 100% identity) to a portion of the SlFSR gene or a transcription regulatory region thereof (i.e., at least 60% identity to the sense strand); (b) a second strand having a length of 10 to 100 nucleotides or nucleosides or a combination thereof that is complementary to at least a portion of the first strand; (c) a terminal end overhang; and (d) a ribose modified at a 2' or 3' position, or a deoxyribose modified at a 2' or 3' position, or a combination thereof. In some embodiments, the first strand and/or the second strand have a length of 10 to 50 nucleotides or nucleosides or a combination thereof. In some embodiments, the first strand and/or the second strand have a length of 20 to 30 nucleotides or nucleosides or a combination thereof. In some embodiments, the first strand and/or the second strand have a length of 20 to 25 nucleotides or nucleosides or a combination thereof. In some embodiments, the first strand and/or the second strand have a length of 22 to 26 nucleotides or nucleosides or a combination thereof. In some embodiments, the first strand and/or the second strand have a length of 23 to 25 nucleotides or nucleosides or a combination thereof. In some embodiments, the first strand and/or the second strand have a length of 24 to 26 nucleotides or nucleosides or a combination thereof. In some embodiments, the first strand and/or the second strand have a length of 25 to 30 nucleotides or nucleosides or a combination thereof. In some embodiments, the first strand and/or the second strand have a length of 20 nucleotides or nucleosides or a combination thereof. In some embodiments, the first strand and/or the second strand have a length of 21 nucleotides or nucleosides or a combination thereof. In some embodiments, the first strand and/or the second strand have a length of 22 nucleotides or nucleosides or a combination thereof. In some embodiments, the first strand and/or the second strand have a length of 23 nucleotides or nucleosides or a combination thereof. In some embodiments, the first strand and/or the second strand have a length of 24 nucleotides or nucleosides or a combination thereof. In some embodiments, the first strand and/or the second strand have a length of 25 nucleotides or nucleosides or a combination thereof. In some embodiments, the first strand and/or the second strand have a length of 26 nucleotides or nucleosides or a combination thereof. In some embodiments, the first strand and/or the second strand have a length of 27 nucleotides or nucleosides or a combination thereof. In some embodiments, the first strand and/or the second strand have a length of 28 nucleotides or nucleosides or a combination thereof. In some embodiments, the first strand and/or the second strand have a length of 29 nucleotides or nucleosides or a combination thereof. In some embodiments, the first strand and/or the second strand have a length of 30 nucleotides or nucleosides or a combination thereof. In some embodiments, the first strand and the second strand are the same length.

In some embodiments of the artificial nucleic acid constructs provided herein, the terminal end overhang is one nucleotide or nucleoside in length. In some embodiments, the terminal end overhang is a 3' end overhang. In some embodiments, the artificial nucleic acid construct comprises two 3' end overhangs. In some embodiments, one or both 3' end overhangs are one nucleotide or nucleoside in length.

In some instances, the first strand of the artificial nucleic acid construct comprises at least about 60%, 65%, 70%, 75%, 80%, 85%, 90%, 91%, 92%, 93%, 94%, 95%, 96%, 97%, 98%, 99%, 99.5%, 99.9%, or 100% sequence identity to a portion of the SlFSR gene or a transcription regulatory region thereof (e.g., at least about 60% identity to the sense strand). In some instances, the first strand of the artificial nucleic acid construct comprises at least about 60%, 65%, 70%, 75%, 80%, 85%, 90%, 91%, 92%, 93%, 94%, 95%, 96%, 97%, 98%, 99%, 99.5%, 99.9%, or 100% sequence identity to a portion of the SlFSR gene or a transcription regulatory region thereof, wherein the portion is the same length as the first strand. In some instances, the first strand of the artificial nucleic acid construct comprises at least about 60%, 65%, 70%, 75%, 80%, 85%, 90%, 91%, 92%, 93%, 94%, 95%, 96%, 97%, 98%, 99%, 99.5%, 99.9%, or 100% sequence identity to a portion of a transcription regulatory region of the SlFSR gene.

In some instances, the second strand of the artificial nucleic acid construct comprises at least about 60%, 65%, 70%, 75%, 80%, 85%, 90%, 91%, 92%, 93%, 94%, 95%, 96%, 97%, 98%, 99%, 99.5%, 99.9%, or 100% sequence identity to the reverse complement of a portion of the SlFSR gene or a transcription regulatory region thereof (e.g., at least about 60% identity to the antisense strand). In some instances, the second strand of the artificial nucleic acid construct comprises at least about 60%, 65%, 70%, 75%, 80%, 85%, 90%, 91%, 92%, 93%, 94%, 95%, 96%, 97%, 98%, 99%, 99.5%, 99.9%, or 100% sequence identity to the reverse complement of a portion of the SlFSR gene or a transcription regulatory region thereof, wherein the portion is the same length as the second strand. In some instances, the second strand of the artificial nucleic acid construct comprises at least about 60%, 65%, 70%, 75%, 80%, 85%, 90%, 91%, 92%, 93%, 94%, 95%, 96%, 97%, 98%, 99%, 99.5%, 99.9%, or 100% sequence identity to a reverse complement of a portion of a transcription regulatory region of the SlFSR gene.

In some embodiments, the second strand of the artificial nucleic acid construct comprises a nucleic acid sequence that is complementary to at least a portion of the first strand. In some embodiments, the first strand and the second strand are perfectly complementary aside from the terminal end overhang(s). For example, the first strand and the second strand may be complementary to overlapping but offset portions of the sense and antisense strands of the SlFSR gene or a transcription regulatory region thereof. In some embodiments, the first strand and the second strand have a length of 20-30 (e.g., 24) nucleotides or nucleosides or a combination thereof, wherein the first strand and the second strand are perfectly complementary aside from a one nucleotide or nucleoside 3' terminal end overhang on the first strand and the second strand.

In some embodiments, the transcription regulatory region is within the SlFSR gene body, upstream of the SlFSR gene (i.e., within 50 kB upstream of the transcription start site), or downstream of the SlFSR gene (i.e., within 50 kB downstream of the transcription termination site). In some embodiments, the transcription regulatory region is further away from the SlFSR gene (e.g., further than 50 kB upstream of the transcription start site, further than 50 kB downstream of the transcription termination site, or located on a different chromosome). In some embodiments, the transcription regulatory region is a 1.0 kB region upstream of the translation start site of the SlFSR gene. In some embodiments, the transcription regulatory region is a 0.5 kB region upstream of the translation start site of the SlFSR gene.

In some embodiments, the first strand and/or the second strand of the artificial nucleic acid constructs provided herein comprise at least about 10%, 15%, 20%, 25%, 30%, 35%, 40%, 45%, 50%, 55%, 60%, 65%, 70%, 75%, 80%, 85%, or 90% guanine-cytosine content (GC content). In some embodiments, the first strand and/or the second strand comprise at least about 20% GC content. In some embodiments, the first strand and/or the second strand comprise at least about 25% GC content. In some embodiments, the first strand and/or the second strand comprise at least about 30% GC content.

In some instances, the first strand and/or the second strand of the artificial nucleic acid constructs provided herein comprise at least about 60%, 65%, 70%, 75%, 80%, 85%, 90%, 91%, 92%, 93%, 94%, 95%, 96%, 97%, 98%, 99%, 99.5%, 99.9%, or 100% sequence identity to any one of SEQ ID NOs: 1-82, which are listed in Table 1. In some embodiments, the first strand comprises any of the sequences shown in the "First strand" column in Table 1. In some embodiments, the second strand comprises any of the sequences shown in the "Second strand" column in Table 1. In some embodiments of the artificial nucleic acid constructs provided herein, the first strand comprises one of the sequences shown in the "First strand" column in Table 1, and the second strand comprises the sequence shown in the "Second strand" column in the same row in Table 1 (mC=2'-O-methyl cytosine, mG=2'-O-methyl guanine, mA=2'-O-methyl adenine, mT=2'-O-methyl thymine, mU=2'-O-methyl uracil).

TABLE 1

Exemplary first strand and second strand nucleic acid sequences.

| First strand | Second strand |
|---|---|
| 1600_f<br>TTCATCCTTATCAGAGGTCTTCGmG<br>(SEQ ID NO: 1) | 1600_f rev<br>CGAAGACCTCTGATAAGGATGAAmA<br>(SEQ ID NO: 2) |
| 1625_f<br>TCGAGCTCTGGGTATGGACAAAAmU<br>(SEQ ID NO: 3) | 1625_f rev<br>TTTTGTCCATACCCAGAGCTCGAmA<br>(SEQ ID NO: 4) |
| 1650_f<br>GCTACTCCTGAATGGGCCCTATAmU<br>(SEQ ID NO: 5) | 1650_f rev<br>TATAGGGCCCATTCAGGAGTAGCmG<br>(SEQ ID NO: 6) |
| 1675_f<br>GTGCGCCATCCAAATTTAATCGGmG<br>(SEQ ID NO: 7) | 1675_f rev<br>CCGATTAAATTTGGATGGCGCACmU<br>(SEQ ID NO: 8) |

TABLE 1-continued

Exemplary first strand and second strand nucleic acid sequences.

| First strand | Second strand |
|---|---|
| 1700_f CTCTAATATGGTCTCCGAACAACmG (SEQ ID NO: 9) | 1700_f rev GTTGTTCGGAGACCATATTAGAGmC (SEQ ID NO: 10) |
| 1725_f ATAAAAAAAAAAACTGTTCACCAmA (SEQ ID NO: 11) | 1725_f rev TGGTGAACAGTTTTTTTTTTTATmG (SEQ ID NO: 12) |
| 1750_f CTTTTGGTGGTTAGCAAAATTTGmG (SEQ ID NO: 13) | 1750_f rev CAAATTTTGCTAACCACCAAAAGmG (SEQ ID NO: 14) |
| 1775_f AATCAATTTACTTGATGAAGTTCmU (SEQ ID NO: 15) | 1775_f rev GAACTTCATCAAGTAAATTGATTmA (SEQ ID NO: 16) |
| 1800_f TAAAGTAATATTATTCCACACACmC (SEQ ID NO: 17) | 1800_f rev GTGTGTGGAATAATATTACTTTAmG (SEQ ID NO: 18) |
| 1825_f AAGAGTATTCAAATTTGAATTCCmC (SEQ ID NO: 19) | 1825_f rev GGAATTCAAATTTGAATACTCTTmU (SEQ ID NO: 20) |
| 1850_f TCAAATAGAAAAAAGAATGAAAAmA (SEQ ID NO: 21) | 1850_f rev TTTTCATTCTTTTTTCTATTTGAmA (SEQ ID NO: 22) |
| 1875_f AGGTTAATTACTTAATATGAAAAmA (SEQ ID NO: 23) | 1875_f rev TTTTCATATTAAGTAATTAACCTmG (SEQ ID NO: 24) |
| 1900_f CTGAATTAGATTTCAAGCTTATAmG (SEQ ID NO: 25) | 1900_f rev TATAAGCTTGAAATCTAATTCAGmU (SEQ ID NO: 26) |
| 1925_f GACTAGGTCCTTATAGTACATGCmA (SEQ ID NO: 27) | 1925_f rev GCATGTACTATAAGGACCTAGTCmU (SEQ ID NO: 28) |
| 1950_f GTTAATTAATCTAATATTTTAGGmG (SEQ ID NO: 29) | 1950_f rev CCTAAAATATTAGATTAATTAACmA (SEQ ID NO: 30) |
| 1975_f GAATTTATAGAGTTCTAACTTGGmU (SEQ ID NO: 31) | 1975_f rev CCAAGTTAGAACTCTATAAATTCmA (SEQ ID NO: 32) |
| 2000_f CATATAGCTAGAGATCTTCAAATmC (SEQ ID NO: 33) | 2000_f rev ATTTGAAGATCTCTAGCTATATGmG (SEQ ID NO: 34) |
| 2025_f AACAAACAATTTTGTTTGCTAACmA (SEQ ID NO: 35) | 2025_f rev GTTAGCAAACAAAATTGTTTGTTmU (SEQ ID NO: 36) |
| 2050_f AACAGTAAGAAAGTAATTGGGTAmA (SEQ ID NO: 37) | 2050_f rev TACCCAATTACTTTCTTACTGTTmU (SEQ ID NO: 38) |
| 2075_f GAGAATGTTAAAATCTCTGACCAmU (SEQ ID NO: 39) | 2075_f rev TGGTCAGAGATTTTAACATTCTCmC (SEQ ID NO: 40) |
| 2100_f TTATTTAAACGTTTAAGTTATTAmA (SEQ ID NO: 41) | 2100_f rev TAATAACTTAAACGTTTAAATAAmG (SEQ ID NO: 42) |
| 2125_f TAAAGCAATTTTTTATTTATTTAmU (SEQ ID NO: 43) | 2125_f rev TAAATAAATAAAAAATTGCTTTAmU (SEQ ID NO: 44) |
| 2150_f TTTTGTTTAACACGACTCTTCACmC (SEQ ID NO: 45) | 2150_f rev GTGAAGAGTCGTGTTAAACAAAAmA (SEQ ID NO: 46) |

TABLE 1-continued

Exemplary first strand and second strand nucleic acid sequences.

| First strand | Second strand |
|---|---|
| 2175_f<br>GCAGACCTAATTATTTTTTTTCAmU<br>(SEQ ID NO: 47) | 2175_frev<br>TGAAAAAAAATAATTAGGTCTGCmG<br>(SEQ ID NO: 48) |
| 2200_f<br>GTTCAAGCTTGTGAAATTTCTTTmU<br>(SEQ ID NO: 49) | 2200_f rev<br>AAAGAAATTTCACAAGCTTGAACmU<br>(SEQ ID NO: 50) |
| 2225_f<br>GATACTCCTGATCAATCTCTACTmU<br>(SEQ ID NO:51) | 2225_f rev<br>AGTAGAGATTGATCAGGAGTATCmA<br>(SEQ ID NO: 52) |
| 2250_f<br>CTCTGGTACTATATTGAAATACAmU<br>(SEQ ID NO: 53) | 2250_f rev<br>TGTATTTCAATATAGTACCAGAGmC<br>(SEQ ID NO: 54) |
| 2275_f<br>GAATATATTCCAGCCGTATATATmA<br>(SEQ ID NO: 55) | 2275_f rev<br>ATATATACGGCTGGAATATATTCmG<br>(SEQ ID NO: 56) |
| 2300_f<br>TAGTAGTACTCTTTCACTAATCCmC<br>(SEQ ID NO: 57) | 2300_f rev<br>GGATTAGTGAAAGAGTACTACTAmA<br>(SEQ ID NO: 58) |
| 2325_f<br>CTCTCTTTTCTTGGATTACTTAAmA<br>(SEQ ID NO: 59) | 2325_f rev<br>TTAAGTAATCCAAGAAAAGAGAGmA<br>(SEQ ID NO: 60) |
| 2350_f<br>ATATCTTTGCTTCATCTATATATmA<br>(SEQ ID NO:61) | 2350_f rev<br>ATATATAGATGAAGCAAAGATATmG<br>(SEQ ID NO: 62) |
| 2375_f<br>AAGATATATCTCCAGTCTGATTAmC<br>(SEQ ID NO: 63) | 2375_f rev<br>TAATCAGACTGGAGATATATCTTmA<br>(SEQ ID NO: 64) |
| 2400_f<br>CATTTTCTTCCATATTTTTCTTCmA<br>(SEQ ID NO: 65) | 2400_f rev<br>GAAGAAAAATATGGAAGAAAATGmA<br>(SEQ ID NO: 66) |
| 2425_f<br>ACTTACATGCACGTACATAAAACmA<br>(SEQ ID NO: 67) | 2425_f rev<br>GTTTTATGTACGTGCATGTAAGTmU<br>(SEQ ID NO: 68) |
| 2450_f<br>AACCTTACATATTTTTTTAATTCmC<br>(SEQ ID NO: 69) | 2450_f rev<br>GAATTAAAAAAATATGTAAGGTTmU<br>(SEQ ID NO: 70) |
| 2475_f<br>TATATATAATACTTAGTCATACAmU<br>(SEQ ID NO: 71) | 2475_f rev<br>TGTATGACTAAGTATTATATATAmA<br>(SEQ ID NO: 72) |
| 2500_f<br>ACTCCATCATGAAAAAGGAAATCmC<br>(SEQ ID NO: 73) | 2500_f rev<br>GATTTCCTTTTTCATGATGGAGTmG<br>(SEQ ID NO: 74) |
| 2525_f<br>ATTTCAGTAAGACTTGATCTGATmC<br>(SEQ ID NO: 75) | 2525_f rev<br>ATCAGATCAAGTCTTACTGAAATmA<br>(SEQ ID NO: 76) |
| 2550_f<br>ATCGTATAGTTTAGATTCAAGTTmG<br>(SEQ ID NO: 77) | 2550_f rev<br>AACTTGAATCTAAACTATACGATmU<br>(SEQ ID NO: 78) |
| 2575_f<br>TCGTTGCTTCCATTTTATTGTGTmU<br>(SEQ ID NO: 79) | 2575_f rev<br>ACACAATAAAATGGAAGCAACGAmC<br>(SEQ ID NO: 80) |
| 2600_f<br>ATCATTATACATAGTAGAGTCAAmG<br>(SEQ ID NO: 81) | 2600_f rev<br>TTGACTCTACTATGTATAATGATmA<br>(SEQ ID NO: 82) |

In some instances, the nucleic acid construct may comprise at least one modified sugar, e.g. a ribose modified at a 2' or 3' position, or a deoxyribose modified at a 2' or 3' position, or a combination thereof. In some embodiments, the nucleic acid may comprise one or more modified ribose sugars (e.g., one or more ribose sugars modified at a 2' or 3' position). In some embodiments, the nucleic acid may comprise one or more modified deoxyribose sugars (e.g., one or more deoxyribose sugars modified at a 2' or 3' position). In some embodiments, the nucleic acid construct may comprise one or more modified ribose sugars and one or more modified deoxyribose sugars. Numbering of a nucleotide sugar should be understood to follow normal conventions of positional numbering in the art. In some instances, the modified sugar may comprise a 2'-R, 2'-0-R, 3'-R, or 3'-0-R group. In some instances, the R group may be selected from the group consisting of alkyl, aryl, haloalkyl, amino, and halogen. In some instances, the R group can be a fluoro (F). In some instances, the R group can be an ethoxy ethyl. In some instances, the R group can be methyl. In some instances, R can be $—(C═O)_n—R1$. In some embodiments, the R group is selected from the group consisting of: an alkyl, an aryl, a haloalkyl, an amino, a methyl, an acetyl, and a halo. In some embodiments, the R group is a methyl.

Unless otherwise indicated, whenever there is a stereocenter in a structure disclosed or illustrated herein, the stereocenter can be R or S in each case.

The term "amino" can refer to functional groups that contain a basic nitrogen atom with a lone pair. For example, an amino can include the radical

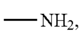, 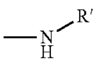, or 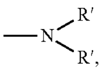, wherein each R' is independently H, halo, alkyl, aryl, heteroalkyl, arylalkyl, heteroaryl, heteroarylalkyl, cycloalkyl, or heterocycloalkyl.

The term "halo" or "halogen" can refer to fluorine, chlorine, bromine or iodine or a radical thereof.

The term "alkyl" can refer to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl; and the like.

The term "aryl" can refer to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2, 4-diene, pentacene, pentalene, pentaphene, perylene, phenalene, phenanthrene, picene, pleiadene, pyrene, pyranthrene, rubicene, triphenylene, trinaphthalene and the like. In certain instances, an aryl group comprises from 6 to 20 carbon atoms.

The terms "heteroalkyl, heteroalkanyl, heteroalkenyl, heteroalkynyl" refer to alkyl, alkanyl, alkenyl and alkynyl groups, respectively, in which one or more of the carbon atoms (and any associated hydrogen atoms) are each independently replaced with the same or different heteroatomic groups. Typical heteroatomic groups include, but are not limited to, —O—, —S—, —O—O', —S—S—, —O—S—, —NR'—, ═N—N═, —N═N—, —N═N—NR'—, —PH—, —P(O)2-, —O—P(O)2-, —S(O)—, —S(O)2-, —SnH2- and the like, wherein R' is hydrogen, alkyl, substituted alkyl, cycloalkyl, substituted cycloalkyl, aryl or substituted aryl.

The term "substituted" can refer to a group in which one or more hydrogen atoms are each independently replaced with the same or different substituent(s). Typical substituents include, but are not limited to halo, alkyl, aryl, heteroalkyl, arylalkyl, heteroaryl, heteroarylalkyl, cycloalkyl, and heterocycloalkyl.

In some embodiments, the ribose modified at a 2' or 3' position, or the deoxyribose modified at a 2' or 3' position, or the combination thereof (e.g., a ribose modified at a 2' or 3' position and a deoxyribose modified at a 2' or 3' position) are at a terminal nucleotide or nucleoside of the first strand and/or the second strand of the artificial nucleic acid construct. In some embodiments, the ribose modified at a 2' or 3' position, or the deoxyribose modified at a 2' or 3' position, or the combination thereof are at a 3' terminal nucleotide or nucleoside of the first strand and the second strand of the artificial nucleic acid construct. In some embodiments, the ribose modified at a 2' or 3' position, or the deoxyribose modified at a 2' or 3' position, or the combination thereof comprises a 2'-O—R group.

The artificial nucleic acid constructs may comprise one or more modifications, such as a chemical modification. An artificial nucleic acid construct may comprise about: 1, 2, 3, 4, 5, 6, 7, 8, 9, 10, 11, 12, 13, 14, 15, 16, 17, 18, 19, 20, 25, 30, 35 modifications or more. An artificial nucleic acid construct may comprise from about 1 to about 10 modifications. An artificial nucleic acid construct may comprise from about 1 to about 20 modifications. An artificial nucleic acid construct may comprise from about 5 to about 20 modifications. A modification may be added to an artificial nucleic acid construct to enhance stability of the construct, such as when delivered in vivo. A modification may be added to an artificial nucleic acid construct to enhance uptake of the construct, such as when delivered in vivo. A portion of bases of an artificial nucleic acid construct may comprise a modification, such as about 10%, 20%, 30%, 40%, 50%, 60%, 70%, 80%, 90% of bases or more. In some embodiments, a modification can comprise addition of a methyl group, a fluoro group, a phosphorothioate backbone, or any combination thereof.

Additional properties of nucleic acid constructs that may be useful in the methods described herein are described in more detail in PCT Appl. No. WO2020191072A1.

Use of the artificial nucleic acid constructs described herein has several advantages. The specifically designed oligonucleotides can introduce cytosine methylation at a defined region of a plant genome, which can control transcript expression levels. The nucleic acid constructs can be introduced by application to the seed coat or to the growing roots of a plant (e.g., a tomato plant), enabling rapid construction of plants with tailored gene expression profiles. In some embodiments, the modified bases (e.g., methylated cytosines) are heritable, enabling generation of parental breeding lines with desired expression profiles. Thus, methylation and altered transcript levels can be propagated through future progeny generations. Additionally, the application of nucleic acid constructs to plants can be multiplexed by application of mixtures of nucleic acid constructs having unique targeting sequences, such that multiple transcription regulatory regions of a gene, and/or multiple genes, may be targeted simultaneously.

In some embodiments, the artificial nucleic acid constructs described herein facilitate an epigenetic modification at the SlFSR gene or a transcription regulatory region thereof through a system that at least in part comprises an enzyme or a fragment thereof. In some embodiments, an enzyme or fragment thereof may catalyze a transfer of a methyl group to at least one base of a nucleic acid sequence, such as a portion of the SlFSR gene or a transcription regulatory region thereof. In some cases, an enzyme or fragment thereof may comprise a methyltransferase. In some cases, an enzyme or fragment thereof may comprise a methyltransferase (MET), a chromomethyltransferase (CMT), a domain rearranged methyltransferase (DRM), any catalytically active fragment thereof, or any combination thereof. In some cases, an enzyme or fragment thereof may comprise Dnmt3a, Dnmt3b, Dnmt3L, DRM1, DRM2, NtDRMl, Zmet3, Fmu, Dnmtl, METl, DIM2, DRM2, CMT1, CMT3, any catalytically active fragment thereof, or any combination thereof. A CMT enzyme may comprise OsCMT3, ZCMT3, OsCMTl, NtCMTl, CMT3, any catalytically active fragment thereof or any combination thereof. A MET enzyme may comprise NtMETl, OsMETl-2, ZMET1, OsMETl-1, METl, any catalytically active fragment thereof, or any combination thereof. A DRM enzyme may comprise OsDRM3, OsDRM2, OsDRMla, OsDRMlb, ZMET3, NtDRMl, DRMl, DRM2, any catalytically active fragment thereof, or any combination thereof. A DNMT2 enzyme may comprise OsDNMT2, ZMET4, OsCMT2, any catalytically active fragment thereof, or any combination thereof. A nucleic acid sequence (e.g., within the SlFSR gene or a transcription regulation region thereof) may be contacted with any of the forgoing enzymes or fragments thereof thereby yielding an epigenetic modification of at least one base in a nucleic acid sequence. Compositions as described herein, including nucleic acid constructs, may guide endogenous enzymes or fragments thereof to a base of interest in a nucleic acid sequence and thereby direct the contact of the enzyme or fragment thereof with the base of interest such that the enzyme or fragment thereof performs epigenetic modification of the base of interest. "Endogenous" should be understood to mean naturally occurring within the organism that contains the gene. Thus, an "endogenous" epigenetic modifying enzyme should be understood to mean a modifying enzyme that is naturally present in the organism that contains the gene.

Methods as described herein may comprise inducing methylation of one or more bases of a nucleic acid sequence, such as a portion of the SlFSR gene or a transcription regulatory region thereof. Methods as described herein may comprise oxidizing one or more bases of a nucleic acid sequence, such as a portion of the SlFSR gene or a transcription regulatory region thereof. Methods as described herein may comprise epigenetically modifying at least one base of a nucleic acid sequence, said epigenetic modification being heritable to a plant progeny.

In some cases, an enzyme or fragment thereof may catalyze a change in an epigenetic modification of at least one base of a nucleic acid sequence (such as a portion of the SlFSR gene or a transcription regulatory region thereof). A change in an epigenetic modification may include a conversion of a methylated base to a hydroxymethylated base, a carboxylated base, a formylated base, or a combination of any of these. In some cases, an enzyme may comprise a dioxygenase. In some cases, an enzyme may comprise a ten-eleven translocation (TET) family enzyme. In some cases, an enzyme may comprise TET1, TET2, TET3, CXXC finger protein 4 (CXXC4), any catalytically active fragment thereof, or any combination thereof.

An epigenetic modification may occur at any base, such as a cytosine, a thymine, a uracil, an adenine, a guanine, or any combination thereof. The epigenetic modifications described herein may be a heritable epigenetic modification, such as an epigenetic modification passed to at least one progeny of an organism. The epigenetic modification may be an engineered epigenetic modification, such as an epigenetic modification that is not non-naturally occurring at a particular base in a nucleic acid sequence of a native organism but one that is introduced into the organism or into an ancestor of an organism using a method as described herein. An organism may comprise a heritable epigenetic modification that may have been previously introduced into a parent organism or an ancestor organism that is retained for at least one reproduction cycle.

In some cases, an epigenetic modification may comprise an oxidation or a reduction. A nucleic acid sequence may comprise one or more epigenetically modified bases. An epigenetically modified base may comprise any base, such as a cytosine, a uracil, a thymine, adenine, or a guanine. An epigenetically modified base may comprise a methylated base, a hydroxymethylated base, a formylated base, or a carboxylic acid containing base or a salt thereof. An epigenetically modified base may comprise a 5-methylated base, such as a 5-methylated cytosine (5-mC). An epigenetically modified base may comprise a 5-hydroxymethylated base, such as a 5-hydroxymethylated cytosine (5-hmC). An epigenetically modified base may comprise a 5-formylated base, such as a 5-formylated cytosine (5-fC). An epigenetically modified base may comprise a 5-carboxylated base or a salt thereof, such as a 5-carboxylated cytosine (5-caC).

In some embodiments, the artificial nucleic acid constructs described herein facilitate an epigenetic modification at the SlFSR gene or a transcription regulatory region thereof through a system that at least in part comprises a DNA methyltransferase, a biologically active fragment thereof, or a derivative thereof. In some embodiments, the system comprises at least a portion of at least one component of an RNA directed DNA methylation pathway. In some embodiments, the at least one component of an RNA directed DNA methylation pathway comprises a protein or a portion thereof. In some embodiments, the protein or portion thereof is an enzyme or a portion thereof.

In some embodiments, the epigenetic modification comprises addition of a chemical group to at least one base of a nucleotide or nucleoside in a nucleic acid sequence at the SlFSR gene or a transcription regulatory region thereof. In some embodiments, the at least one base is a cytosine. In some embodiments, the at least one base is part of a CpG island. In some embodiments, the chemical group comprises a methyl group.

Also disclosed herein are pluralities of any of the artificial nucleic acid constructs described above. In some embodiments, the plurality comprises at least about: 2-125, 2-110, 2-105, 2-100, 2-90, 2-80, 2-70, 2-60, 2-50, 2-40, 2-30, 2-24, 2-20, 2-12, 4-100, 4-90, 4-80, 4-70, 4-60, 4-50, 4-40, 4-30, 4-24, 4-12, 6-100, 6-90, 6-80, 6-70, 6-60, 2-50, 6-40, 6-30, 6-24, 6-12, 8-100, 8-90, 8-80, 8-70, 8-60, 8-50, 8-40, 8-30, 8-24, 8-12, 10-125, 10-110, 10-105, 10-100, 10-90, 10-80, 10-70, 10-60, 10-50, 10-40, 10-30, 10-24, or 10-12 of the artificial nucleic acid constructs described herein. In some embodiments, the plurality comprises at least about 2-125 of the artificial nucleic acid constructs described herein. In some embodiments, the plurality comprises at least about 2-50 of the artificial nucleic acid constructs described herein.

In some embodiments, the plurality comprises at least some artificial nucleic acid constructs having a first strand comprising at least 90% identity to more than one different portion of the SlFSR gene or a transcription regulatory region thereof. In some embodiments, each artificial nucleic acid construct in the plurality has a first strand comprising at least 90% identity to a different portion of the SlFSR gene or a transcription regulatory region thereof. In some instances, at least about 10% to about 100% of the number of the artificial nucleic acid constructs in the plurality comprise different nucleic acid sequences. In some instances, all of the artificial nucleic acid constructs in the plurality comprise different nucleic acid sequences. In some embodiments, artificial nucleic acid constructs in the plurality specifically bind to different nucleic acid sequences within the SlFSR gene or a transcription regulatory region thereof. In some embodiments, all of the artificial nucleic acid constructs in the plurality comprise the same nucleic acid sequence (i.e. the same first stand and the same second strand). In such embodiments, all of the artificial nucleic acid constructs have at least 90% identity to the same portion of the SlFSR gene or a transcription regulatory region thereof. In such embodiments, all of the artificial nucleic acid constructs bind specifically to the sequence of the same portion of the SlFSR gene or a transcription regulatory region thereof.

Also disclosed herein are formulations comprising at least one artificial nucleic acid construct as described above. In some embodiments, the formulation comprises a plurality of the artificial nucleic acid construct as described above. In some embodiments, the formulation is a liquid. In some embodiments, the formulation is a solid. In some embodiments, the formulation is a semi-solid substance. In some embodiments, the formulation is a suspension. In some embodiments, the formulation comprises water. In some embodiments, each artificial nucleic acid construct in the formulation is present in equal (or relatively equal, e.g., substantially equal) amounts. In some embodiments, each artificial nucleic acid construct in the formulation is present at a concentration of about 1 μM to about 500 μM (e.g. about 1 μM to about 400 μM, about 5 μM to about 350 μM, about 10 μM to about 300 μM, about 100 μM to about 300 μM, about 150 μM, about 200 μM, about 250 μM, or about 300 μM). In some embodiments, each artificial nucleic acid construct in the formulation is present at a concentration of about 250 μM. In some embodiments, the formulations further comprise a tomato plant or any constituent part thereof (e.g., a tomato fruit or a tomato seed).

In some embodiments, the formulations described herein are suitable as a seed treatment. In some embodiments, the formulation is a powder, granule, pellet, bead, or liquid. In some embodiments, the formulation is a liquid (e.g., a solution comprising the artificial nucleic acid constructs in an aqueous solution, such as water), and one or more tomato seeds can be brought into contact with the liquid (e.g., fully or partially submerged in the liquid or kept in contact with an absorbent substrate comprising the formulation), as described above. In some embodiments, the formulation can be applied to a tomato plant as a seed treatment, soil drench, granule formulation, or foliar spray, e.g., to extend the shelf life of a tomato fruit produced from a modified tomato plant. In some embodiments The formulations may comprise at least about 0.1% (w/w) of an nucleic acid construct, plant, or constituent part thereof, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the nucleic acid construct, plant, or constituent part thereof.

The formulations may comprise less than about 95% (w/w) of an nucleic acid construct, plant, or constituent part thereof, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the nucleic acid construct, plant, or constituent part thereof.

The formulations may comprise about 0.1%-100% (w/w) of a nucleic acid construct, plant, or constituent part thereof, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of the nucleic acid construct, plant, or constituent part thereof.

Unless otherwise indicated, formulations herein can contain water in an amount from about 0% to about 99% w/w, for example about: 0-10%, 0-5%, or 0-1% w/w; or less than about: 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90% or 99% w/w, based on the weight of the formulation.

In some embodiments, the formulations comprise one or more additives. In some cases, the formulations comprise one or more additives to facilitate nucleic acid delivery. In some instances, the additive may be a low or high molecular weight polyamine. In some instances, the additive may be polyethylenimine (PEI). In some instances, the additive may be a polyamidoamine (PAMAM) dendrimer. In some instances, the peptide may be a derivative of a viral protein. In some instances, the additive may be a cationic peptide. In some instances, the additive may be an arginine rich peptide (e.g. TAT). In some instances, the additive may be histidine rich peptide (e.g. endoporter). In some instances, the additive may be a lytic peptide (e.g. melittin).

In some embodiments, the formulations comprise one or more plant growth regulators (PGRs). In some embodiments, the formulations comprise one or more salts or solvates thereof. In some embodiments, the formulations comprise one or more fertilizers. In some embodiments, the formulations comprise one or more PGRs, salts, or solvates. PGRs can be numerous chemical substances that can influence the growth and/or differentiation of plant cells, tissues, or organs. Plant growth regulators can function as chemical messengers for intercellular communication. PGRs can include auxins, gibberellins, cytokinins, abscisic acid (ABA) and ethylene, brassinosteroids, and polyamines. They can work together coordinating the growth and/or development of cells. PGRs can elicit hydraulic enhancement of a plant. PGRs can increase the harvest yield of a plant. Auxins can comprise indole-3-acetic acid (IAA) or its derivative or chemical analog.

In some cases, the formulations disclosed herein may further comprise one or more additives to facilitate nucleic acid delivery. In some instances, the additive may be a low or high molecular weight polyamine. In some instances, the additive may be polyethylenimine (PEI). In some instances, the additive may be a polyamidoamine (PAMAM) dendrimer. In some instances, the peptide may be a derivative of a viral protein. In some instances, the additive may be a cationic peptide. In some instances, the additive may be an arginine rich peptide (e.g. TAT). In some instances, the additive may be histidine rich peptide (e.g. endoporter). In some instances, the additive may be a lytic peptide (e.g. melittin).

In some embodiments, the formulations disclosed herein may further comprise one or more excipients. The one or more excipients can be one or more stabilizers, one or more additives, one or more carriers, one or more dispersants, one or more fertilizers, or any combination thereof. In one example, one or more excipients comprise acetone. In some embodiments, the one or more excipients comprise water.

In some embodiments, the formulations disclosed herein may further comprise one or more stabilizers and/or other additives. The stabilizers and/or additives can include, but are not limited to, penetration agents, adhesives, anticaking agents, dyes, dispersants, wetting agents, emulsifying agents, defoamers, antimicrobials, antifreeze, pigments, colorants, buffers, and carriers. The formulations may further comprise surfactants and/or adjuvants.

In some embodiments, the formulations disclosed herein may further comprise one or more carriers. Examples of carriers include, but are not limited to, solid carriers, sponges, textiles, and synthetic materials. The synthetic material may be a porous synthetic material. Additional carriers can include organic carriers, such as waxes, linolin, paraffin, dextrose granules, sucrose granules and maltose-dextrose granules. Alternatively, the carrier can be an an organic carrier such as natural clays, kaolin, pyrophyllite, bentonite, alumina, montmorillonite, kieselguhr, chalk, diatomaceous earths, calcium phosphates, calcium and magnesium carbonates, sulphur, lime, flours or tale. The formulation may be adsorbed into the carrier. The carrier may be characterized by enabling release of the compound, salt, solvate, or formulation.

In some embodiments, the formulations disclosed herein may further comprise one or more dispersants. The dispersant may be a negatively charged anion dispersant. The dispersant may be a nonionic dispersant.

In some embodiments, the formulations disclosed herein may further comprise a fertilizer, nutrient, or other growth additive. The fertilizer may be a chemical fertilizer. The fertilizer may be an organic fertilizer. The fertilizer may be an inorganic fertilizer. The fertilizer may be a granulated or powdered fertilizer. The fertilizer may be a liquid fertilizer. The fertilizer may be a slow-release fertilizer.

Additional properties of the formulations, compositions, and components thereof (e.g., plant growth regulators, salts or solvates thereof, excipients, etc.) that may be useful in the methods described herein are described in more detail in PCT Appl. No. WO2020191072A1.

Also provided herein are compositions comprising a) any of the formulations described above and b) a tomato seed, a tomato plant, a constituent of a tomato plant, or any combination thereof.

D. Methods of Assessing DNA Methylation

In some aspects, an epigenetic modification disclosed herein, such as DNA methylation, can be detected. In some instances, the modification, e.g., methylated nucleotide, may be detected by bisulfite sequencing. Bisulfite treatment may convert a cytosine base to uracil and leave methylated cytosines unconverted. Bisulfite treatment may be applied to a portion of a sample and leave a second portion of the sample untreated. Bisulfite treatment may be performed on a sample prior to sequencing or after sequencing. Bisulfite treatment may be utilized alone or in combination with additional techniques to determine a presence, a pattern or a level of epigenetic modification in a nucleic acid sequence, such as a presence, a pattern or a level of methylation in a sequence.

Bisulfite sequencing may determine a presence, a pattern, or a level of an epigenetic modification in a nucleic acid sequence. Bisulfite-free sequencing may determine a presence, a pattern, or a level of an epigenetic modification in a nucleic acid sequence. A bisulfite treated sequence may be compared to a comparable sequence having not been treated with bisulfite to determine a presence, a pattern, or a level of epigenetic modification in a nucleic acid sequence.

Sequencing (such as bisulfite-free sequencing) may be utilized alone or in combination with additional techniques to determine a presence, a pattern or a level of epigenetic modification in a nucleic acid sequence, such as a presence, a pattern or a level of methylation in a sequence.

Sequencing (such as bisulfite-free sequencing) may determine a presence, a pattern, or a level of an epigenetic modification in a nucleic acid sequence. A treated sequence (such as a sequence having a label added to an epigenetic modification) may be compared to a comparable sequence having not been treated to determine a presence, a pattern, or a level of epigenetic modification in a nucleic acid sequence.

The term "sequencing" as used herein, may comprise bisulfite-free sequencing, bisulfite sequencing, TET-assisted bisulfite (TAB) sequencing, ACE-sequencing, high-throughput sequencing, Maxam-Gilbert sequencing, massively parallel signature sequencing, Polony sequencing, 454 pyrosequencing, Sanger sequencing, Illumina sequencing, SOLiD sequencing, Ion Torrent™ semiconductor sequencing, DNA nanoball sequencing, Heliscope single molecule sequencing, single molecule real time (SMRT™) sequencing, nanopore DNA sequencing, shot gun sequencing, RNA sequencing, Enigma sequencing, or any combination thereof.

In some cases, a method may comprise sequencing. The sequencing may include bisulfite sequencing or bisulfite-free sequencing.

In some instances, the methods may include storing the sample for a time such as, e.g., seconds, minutes, hours, days, weeks, months, years or longer after the sample is obtained and before the sample is analyzed. In some cases, the sample obtained from a subject is subdivided prior to the step of storage or further analysis such that different portions of the sample are subject to different downstream methods or processes including but not limited to any combination of methods described herein, storage, bisulfite treatment, amplification, sequencing, labeling, cytological analysis, adequacy tests, nucleic acid extraction, molecular profiling or a combination thereof.

In some cases, a portion of the sample may be stored while another portion of said sample is further manipulated. Such manipulations may include but are not limited to any method as described herein; bisulfite treatment; sequencing; amplification; labeling; molecular profiling; cytological staining; nucleic acid (RNA or DNA) extraction, detection, or quantification; gene expression product (RNA or Protein) extraction, detection, or quantification; fixation; and examination.

In some instances, a methylated nucleotide may be detected by nanopore sequencing. Nanopores may be used to sequence a sample, a small portion (such as one full gene or a portion of one gene), a substantial portion (such as multiple genes or multiple chromosomes), or the entire genomic sequence of an individual. Nanopore sequencing technology may be commercially available or under development from Sequenom (San Diego, Calif.), Illumina (San Diego, Calif.), Oxford Nanopore Technologies LTD (Kidlington, United Kingdom), and Agilent Laboratories (Santa Clara, Calif.). Nanopore sequencing methods and apparatus are have been described in the art and for example are provided in U.S. Pat. No. 5,795,782, herein incorporated by reference in its entirety.

Nanopore sequencing can use electrophoresis to transport a sample through a pore. A nanopore system may contain an electrolytic solution such that when a constant electric field is applied, an electric current can be observed in the system. The magnitude of the electric current density across a nanopore surface may depend on the nanopore's dimensions and the composition of the sample that is occupying the nanopore. During nanopore sequencing, when a sample approaches and or goes through the nanopore, the samples cause characteristic changes in electric current density across nanopore surfaces, these characteristic changes in the electric current enables identification of the sample. Nanopores used herein may be solid-state nanopores, protein nanopores, or hybrid nanopores comprising protein nanopores or organic nanotubes such as carbon or graphene nanotubes, configured in a solid-state membrane, or like framework. In some instances, nanopore sequencing can be biological, a solid state nanopore or a hybrid biological/solid state nanopore.

In some instances, a biological nanopore can comprise transmembrane proteins that may be embedded in lipid membranes. In some instances, a nanopore described herein may comprise alpha hemolysin. In some instances, a nanopore described herein may comprise *Mycobacterium smegmatis* porin.

Solid state nanopores do not incorporate proteins into their systems. Instead, solid state nanopore technology uses various metal or metal alloy substrates with nanometer sized pores that allow samples to pass through. Solid state nanopores may be fabricated in various materials including but not limited to, silicon nitride (S13N4), silicon dioxide (S1O2), and the like. In some instances, nanopore sequencing may comprise use of tunneling current, wherein a measurement of electron tunneling through bases as sample (ssDNA) translocates through the nanopore is obtained. In some instances, a nanopore system can have solid state pores with single walled carbon nanotubes across the diameter of the pore. In some instances, nanoelectrodes may be used on a nanopore system described herein. In some instances, fluorescence can be used with nanopores, for example solid state nanopores and fluorescence. For example, in such a system the fluorescence sequencing method converts each base of a sample into a characteristic representation of multiple nucleotides which bind to a fluorescent probe strand-forming dsDNA (were the sample comprises DNA). Where a two-color system is used, each base is identified by two separate fluorescence, and will therefore be converted into two specific sequences. Probes may consist of a fluorophore and quencher at the start and end of each sequence, respectively. Each fluorophore may be extinguished by the quencher at the end of the preceding sequence. When the dsDNA is translocating through a solid state nanopore, the probe strand may be stripped off, and the upstream fluorophore will fluoresce.

In some instances, a 1-100 nm channel or aperture may be formed through a solid substrate, usually a planar substrate, such as a membrane, through which an analyte, such as single stranded DNA, is induced to translocate. In other instances, a 2-50 nm channel or aperture is formed through a substrate; and in still other instances, a 2-30 nm, or a 2-20 nm, or a 3-30 nm, or a 3-20 nm, or a 3-10 nm channel or aperture if formed through a substrate.

In some instances, nanopores used in connection with the methods and devices useful herein are provided in the form of arrays, such as an array of clusters of nanopores, which may be disposed regularly on a planar surface. In some instances, clusters are each in a separate resolution limited area so that optical signals from nanopores of different clusters are distinguishable by the optical detection system employed, but optical signals from nanopores within the same cluster cannot necessarily be assigned to a specific nanopore within such cluster by the optical detection system employed.

Disclosed are materials, compositions, and methods that can be used for, can be used in conjunction with or can be used in preparation for the disclosed embodiments. These and other materials are disclosed herein, and it is understood that when combinations, subsets, interactions, groups, etc. of these materials are disclosed that while specific reference of each various individual and collective combinations and permutations of these compositions may not be explicitly disclosed, each is specifically contemplated and described herein. For example, if a method is disclosed and discussed, and a number of modifications that can be made to a number of molecules included in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are various additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties. The following description provides further non-limiting examples of the disclosed compositions and methods.

EXEMPLARY EMBODIMENTS

Exemplary embodiments provided in accordance with the presently disclosed subject matter include, but are not limited to, the claims and the following embodiments:

Embodiment 1 is a modified tomato plant comprising an introduced modification comprising hypermethylation of genomic DNA at a SlFSR gene or a transcription regulatory region thereof.

Embodiment 2 is the modified tomato plant of embodiment 1, wherein the introduced modification is heritable.

Embodiment 3 is the modified tomato plant of embodiment 1 or 2, wherein the hypermethylation is within a 1 kb region upstream of the translation start site of the SlFSR gene.

Embodiment 4 is the modified tomato plant of any one of embodiments 1 to 3, wherein the hypermethylation is within a 0.5 kb region upstream of the translation start site of the SlFSR gene.

Embodiment 5 is the modified tomato plant of any one of embodiments 1 to 4, wherein the modified tomato plant has a reduced expression level of a gene product encoded by the SlFSR gene.

Embodiment 6 is the modified tomato plant of any one of embodiments 1 to 5, wherein the gene product is an mRNA transcript or a protein.

Embodiment 7 is the modified tomato plant of embodiment 5 or 6, wherein the expression level of the gene product is reduced relative to the expression level of the gene product encoded by the SlFSR gene in an unmodified tomato plant.

Embodiment 8 is the modified tomato plant of any one of embodiments 1 to 7, wherein the modified tomato plant is of an heirloom variety.

Embodiment 9 is the modified tomato plant of any one of embodiments 1 to 8, wherein the modified tomato plant is of a Brandywine variety.

Embodiment 10 is the modified tomato plant of any one of embodiments 1 to 8, wherein the modified tomato plant is of a Micro Tom variety.

Embodiment 11 is a modified tomato plant, wherein the modified tomato plant is an offspring of the modified tomato plant of any one of embodiments 1 to 10.

Embodiment 12 is a modified tomato fruit produced by the modified tomato plant of any one of embodiments 1 to 11.

Embodiment 13 is the modified tomato fruit of embodiment 12, wherein the modified tomato fruit has an extended shelf life relative to a tomato fruit produced from an unmodified tomato plant.

Embodiment 14 is the modified tomato fruit of embodiment 12 or 13, wherein the modified tomato fruit retains at least a pre-determined minimum degree of firmness of for at least 14 days.

Embodiment 15 is the modified tomato fruit of any one of embodiments 12 to 14, wherein the modified tomato fruit retains at least a pre-determined minimum degree of for at least 1.3 times as long as an unmodified tomato fruit.

Embodiment 16 is the modified tomato fruit of any one of embodiments 12 to 15, wherein the modified tomato fruit retains an increased degree of firmness relative to an unmodified tomato fruit harvested at the same time at least 7 days after harvesting.

Embodiment 17 is the modified tomato fruit of any one of embodiments 12 to 16, wherein the modified tomato fruit has increased water content relative to an unmodified tomato fruit harvested at the same time at least 7 days after harvesting.

Embodiment 18 is the modified tomato fruit of any one of embodiments 12 to 17, wherein the modified tomato fruit further comprises a coating that reduces ethylene release from the modified tomato fruit or absorbs ethylene released from the modified tomato fruit.

Embodiment 19 is the modified tomato fruit of any one of embodiments 12 to 18, wherein the modified tomato fruit is stored in a climate-controlled environment at a temperature between about 8° C. and about 24° C.

Embodiment 20 is a modified tomato seed produced by the modified tomato plant of any one of embodiments 1 to 11.

Embodiment 21 is a plant produced by growing the modified tomato seed of embodiment 20.

Embodiment 22 is a plant part of the plant of any one of embodiments 1 to 11 or embodiment 21.

Embodiment 23 is the plant part of embodiment 22, wherein the plant part is a leaf, pollen, an ovule, a fruit, a scion, a rootstock, or a cell.

Embodiment 24 is the plant part of embodiment 22 or 23, wherein the plant part is a fruit.

Embodiment 25 is an isolated or cultured cell of the modified tomato plant of any one of embodiments 1 to 11 or 21, the modified tomato fruit of any one of embodiments 12 to 19, the modified tomato seed of embodiment 20, or the plant part of any one of embodiments 22 to 24.

Embodiment 26 is the isolated or cultured cell of embodiment 25, wherein the cell is from an embryo, a meristem, a cotyledon, a pollen, a leaf, an anther, a root, a root tip, a pistil, a flower, a seed, and/or a stalk, optionally wherein the cell is a protoplast.

Embodiment 27 is a population of cells comprising a plurality of the isolated or cultured cells of embodiment 25 or 26.

Embodiment 28 is a method for growing a modified tomato plant, the method comprising growing in a field or an area of cultivation a modified tomato plant of any one of embodiments 1 to 11 or 21 or a seed or seedling thereof.

Embodiment 29 is a method for producing a modified tomato fruit, the method comprising growing in a field or an area of cultivation a modified tomato plant of any one of embodiments 1 to 11 or 21 or a seed or seedling thereof to produce a modified tomato plant and cultivating the modified tomato plant to produce a modified tomato fruit.

Embodiment 30 is the method of embodiment 29, wherein the method further comprises harvesting the modified tomato fruit from the modified tomato plant.

Embodiment 31 is a method for producing the modified tomato plant of any one of embodiments 1 to 11, the method comprising: applying a formulation comprising at least one artificial nucleic acid construct to a tomato seed, a tomato plant, a constituent of a tomato plant, or any combination thereof, each artificial nucleic acid construct comprising a double stranded oligonucleotide comprising: (a) a first strand having a length of 20 to 30 nucleotides or nucleosides, or a combination thereof, and comprising at least 90% identity to a portion of the SlFSR gene or a transcription regulatory region thereof; (b) a second strand having a length of 20 to 30 nucleotides or nucleosides, or a combination thereof, that is complementary to at least a portion of the first strand; (c) a terminal end overhang; and (d) a ribose modified at a 2' or 3' position, or a deoxyribose modified at a 2' or 3' position, or a combination thereof, wherein the at least one artificial nucleic acid construct penetrates the tomato seed, the tomato plant, the constituent of a tomato plant, or any combination thereof and specifically hybridizes to genomic DNA of the tomato seed, the tomato plant, the constituent of a tomato plant, or any combination thereof; and cultivating the tomato seed, the tomato plant, the constituent of a tomato plant, or any combination thereof with the formulation applied for a period of time sufficient to produce the hypermethylation of the genomic DNA of the SlFSR gene or a transcription regulatory region thereof.

Embodiment 32 is the method of embodiment 31, wherein the formulation is applied to a tomato seed.

Embodiment 33 is the method of embodiment 32, wherein the tomato seed is from a modified tomato plant comprising an introduced modification comprising hypermethylation of genomic DNA at a SlFSR gene or a transcription regulatory region thereof.

Embodiment 34 is the method of any one of embodiments 31 to 33, wherein the formulation is a powder, granule, pellet, bead, or liquid.

Embodiment 35 is the method of any one of embodiments 31 to 34, wherein the formulation is a liquid; optionally, wherein the liquid comprises water; optionally, wherein the formulation comprises an excipient; optionally wherein the excipient is water.

Embodiment 36 is the method of any one of embodiments 31 to 35, wherein the first strand and the second strand are the same length.

Embodiment 37 is the method of any one of embodiments 31 to 36, wherein the terminal end overhang is a 3' end overhang.

Embodiment 38 is the method of any one of embodiments 31 to 37, wherein the artificial nucleic acid construct comprises two 3' end overhangs.

Embodiment 39 is the method of any one of embodiments 31 to 38, wherein the ribose modified at a 2' or 3' position, or the deoxyribose modified at a 2' or 3' position, or the combination thereof, are at a terminal nucleotide or nucleoside of the first strand or the second strand of the artificial nucleic acid construct.

Embodiment 40 is the method of any one of embodiments 31 to 38, wherein the ribose modified at a 2' or 3' position, or the deoxyribose modified at a 2' or 3' position, or the combination thereof, are at a 3' terminal nucleotide or nucleoside of the first strand and the second strand of the artificial nucleic acid construct.

Embodiment 41 is the method of any one of embodiments 31 to 40, wherein the ribose modified at a 2' or 3' position, or the deoxyribose modified at a 2' or 3' position, or the combination thereof, comprises a 2'-O—R group.

Embodiment 42 is the method of embodiment 41, wherein the 2'-O—R group is selected from the group consisting of: an alkyl, an aryl, a haloalkyl, an amino, a methyl, an acetyl, and a halo.

Embodiment 43 is the method of embodiment 41 or 42, wherein the 2'-O—R group is a methyl.

Embodiment 44 is the method of any one of embodiments 31 to 43, wherein the first strand comprises at least 90% identity to a portion of a transcription regulatory region of the SlFSR gene within a 1.0 kb region upstream of the translation start site of the SlFSR gene.

Embodiment 45 is the method of any one of embodiments 31 to 44, wherein the first strand comprises at least 90% identity to a portion of a transcription regulatory region of the SlFSR gene within a 0.5 kb region upstream of the translation start site of the SlFSR gene.

Embodiment 46 is the method of any one of embodiments 31 to 45, wherein the first strand and/or the second strand comprises a sequence with at least 90% identity to any of SEQ ID NOs: 1-82.

Embodiment 47 is the method of any one of embodiments 31 to 46, wherein the first strand and/or the second strand comprises a sequence with at least about 30% guanine cytosine (GC) content.

Embodiment 48 is the method of any one of embodiments 31 to 47, wherein the method comprises applying a formulation comprising a plurality of the artificial nucleic acid constructs to the tomato seed, the tomato plant, the constituent of a tomato plant, or any combination thereof.

Embodiment 49 is the method of embodiment 48, wherein the plurality of artificial nucleic acid constructs comprises at least some artificial nucleic acid constructs having a first strand comprising at least 90% identity to different portions of the SlFSR gene or a transcription regulatory region thereof.

Embodiment 50 is the method of embodiment 48 or 49, wherein each artificial nucleic acid construct in the plurality of artificial nucleic acid constructs has a first strand comprising at least 90% identity to a different portion of the SlFSR gene or a transcription regulatory region thereof.

Embodiment 51 is an artificial nucleic acid construct comprising a double stranded oligonucleotide comprising: (a) a first strand having a length of 20 to 30 nucleotides or nucleosides or a combination thereof and comprising at least 90% identity to a portion of the SlFSR gene or a transcription regulatory region thereof; (b) a second strand having a length of 20 to 30 nucleotides or nucleosides or a combination thereof that is complementary to at least a portion of the first strand; (c) a terminal end overhang; and (d) a ribose modified at a 2' or 3' position, or a deoxyribose modified at a 2' or 3' position, or a combination thereof.

Embodiment 52 is the artificial nucleic acid construct of embodiment 51, wherein the first strand and the second strand are the same length.

Embodiment 53 is the artificial nucleic acid construct of embodiment 51 or 52, wherein the terminal end overhang is a 3' end overhang.

Embodiment 54 is the artificial nucleic acid construct of any one of embodiments 51 to 53, wherein the artificial nucleic acid construct comprises two 3' end overhangs.

Embodiment 55 is the artificial nucleic acid construct of any one of embodiments 51 to 54, wherein the ribose modified at a 2' or 3' position, or the deoxyribose modified at a 2' or 3' position, or the combination thereof are at a terminal nucleotide or nucleoside of the first strand and/or the second strand of the artificial nucleic acid construct.

Embodiment 56 is the artificial nucleic acid construct of any one of embodiments 51 to 55, wherein the ribose modified at a 2' or 3' position, or the deoxyribose modified at a 2' or 3' position, or the combination thereof are at a 3' terminal nucleotide or nucleoside of the first strand and the second strand of the artificial nucleic acid construct.

Embodiment 57 is the artificial nucleic acid construct of any one of embodiments 51 to 56, wherein the ribose modified at a 2' or 3' position, or the deoxyribose modified at a 2' or 3' position, or the combination thereof comprises a 2'-O—R group.

Embodiment 58 is the artificial nucleic acid construct of embodiment 57, wherein the 2'-O—R group is selected from the group consisting of: an alkyl, an aryl, a haloalkyl, an amino, a methyl, an acetyl, and a halo.

Embodiment 59 is the artificial nucleic acid construct of embodiment 57 or 58, wherein the 2'-O—R group is a methyl.

Embodiment 60 is the artificial nucleic acid construct of any one of embodiments 51 to 59, wherein the first strand comprises at least 90% identity to an SlFSR transcription regulatory region within a 1.0 kb region upstream of the translation start site of the SlFSR gene.

Embodiment 61 is the artificial nucleic acid construct of any one of embodiments 51 to 60, wherein the first strand comprises at least 90% identity to an SlFSR transcription regulatory region within a 0.5 kb region upstream of the translation start site of the SlFSR gene.

Embodiment 62 is the artificial nucleic acid construct of any one of embodiments 51 to 61, wherein the first strand and/or the second strand comprises a sequence with at least 90% identity to any of SEQ ID NOs: 1-82.

Embodiment 63 is the artificial nucleic acid construct of any one of embodiments 51 to 62, wherein the first strand and/or the second strand comprises a sequence with at least about 30% guanine cytosine (GC) content.

Embodiment 64 is a plurality of artificial nucleic acid constructs comprising at least about 2-125 of the artificial nucleic acid constructs of any one of embodiments 51 to 63.

Embodiment 65 is a plurality of artificial nucleic acid constructs comprising at least about 2-50 of the artificial nucleic acid constructs of any one of embodiments 51 to 63.

Embodiment 66 is the plurality of artificial nucleic acid constructs of embodiment 64 or 65, wherein the plurality comprises at least some artificial nucleic acid constructs having a first strand comprising at least 90% identity to different portions of the SlFSR gene or a transcription regulatory region thereof.

Embodiment 67 is the plurality of any one of embodiments 64 to 66, wherein each artificial nucleic acid construct in the plurality has a first strand comprising at least 90% identity to a different portion of the SlFSR gene or a transcription regulatory region thereof.

Embodiment 68 is a formulation comprising the artificial nucleic acid construct of any one of embodiments 51 to 63 or the plurality of artificial nucleic acid constructs of any one of embodiments 64 to 67.

Embodiment 69 is the formulation of embodiment 68, wherein the formulation is a powder, granule, pellet, bead, or liquid.

Embodiment 70 is the formulation of embodiment 68 or 69, wherein the formulation is a liquid; optionally, wherein the liquid comprises water; optionally, wherein the formulation comprises an excipient; optionally wherein the excipient is water.

Embodiment 71 is the formulation of any one of embodiments 68 to 70, wherein each of the artificial nucleic acid constructs in the plurality are present in the formulation at a concentration of about 250 μM.

Embodiment 72 is a composition comprising a) the formulation of any one of embodiments 68 to 71 and b) a tomato seed, a tomato plant, a constituent of a tomato plant, or any combination thereof.

Embodiment 73 is a seed of tomato plant variety SND-017.

Embodiment 74 is a plant produced by growing the seed of embodiment 73.

Embodiment 75 is a plant part of the plant of embodiment 74.

Embodiment 76 is the plant part of embodiment 75, wherein the plant part is a leaf, pollen, an ovule, a fruit, a scion, a rootstock, or a cell.

Embodiment 77 is the plant part of embodiment 75 or 76, wherein the plant part is a fruit.

Embodiment 78 is a tomato plant, or a part thereof, having all or essentially all the physiological and morphological characteristics of the plant of any one of embodiments 1 to 11, 21, or 74.

Embodiment 79 is an isolated or cultured cell of the plant of embodiment 74 or 78 or the plant part of any one of embodiments 75 to 77.

Embodiment 80 is the isolated or cultured cell according to embodiment 79, wherein the cell is from an embryo, a meristem, a cotyledon, a pollen, a leaf, an anther, a root, a root tip, a pistil, a flower, a seed, and/or a stalk, optionally wherein the cell is a protoplast.

Embodiment 81 is a population of cells comprising a plurality of the isolated or cultured cells of embodiment 79 or 80.

Embodiment 82 is a tomato plant regenerated from the isolated or cultured cell of embodiment 79.

Embodiment 83 is a tomato plant regenerated from the isolated or cultured cell of embodiment 80.

Embodiment 84 is a method of vegetatively propagating the plant of any one of embodiments 1 to 11, 21, 74, 78, 82, or 83, comprising the steps of: (a) collecting tissue capable of being propagated from the plant; (b) cultivating said tissue to obtain proliferated shoots; and (c) rooting said proliferated shoots to obtain rooted plantlets.

Embodiment 85 is the method of embodiment 84, further comprising growing plants from said rooted plantlets.

Embodiment 86 is a method of producing a tomato plant, comprising crossing the plant of any one of embodiments 1 to 11, 21, 74, 78, 82, or 83 with a second tomato plant one or more times, and selecting progeny from said crossing.

Embodiment 87 is a method of introducing a desired trait into a tomato variety comprising: (a) crossing a first plant according to any one of embodiments 1 to 11, 21, 74, 78, 82, or 83 with a tomato plant that comprises a desired trait to produce F1 progeny; (b) selecting an F1 progeny that comprises the desired trait; (c) crossing the selected F1 progeny with a second plant according to any one of embodiments 1 to 11, 21, 74, 78, 82, or 83 to produce backcross progeny; (d) selecting backcross progeny comprising the desired trait and all or essentially all the physiological and morphological characteristics of a plant according to any one of embodiments 1 to 11, 21, 74, 78, 82, or 83; and optionally (e) repeating steps (c) and (d) three or more times in succession to produce selected fourth or higher backcross progeny that comprise the desired trait.

Embodiment 88 is a method of introducing a desired trait into a tomato variety comprising: (a) crossing a first plant of tomato variety SND-017 with a tomato plant that comprises a desired trait to produce F1 progeny; (b) selecting an F1 progeny that comprises the desired trait; (c) crossing the selected F1 progeny with a second plant of tomato variety SND-017 to produce backcross progeny; (d) selecting backcross progeny comprising the desired trait and all or essentially all the physiological and morphological characteristics of tomato variety SND-017; and optionally (e) repeating steps (c) and (d) three or more times in succession to produce selected fourth or higher backcross progeny that comprise the desired trait.

Embodiment 89 is a tomato plant produced by the method of embodiment 86.

Embodiment 90 is a tomato plant produced by the method of embodiment 89.

Embodiment 91 is a tomato plant produced by the method of embodiment 88.

Embodiment 92 is a method of producing a plant comprising an added desired trait, the method comprising introducing a transgene conferring the desired trait into a plant of tomato variety SND-017.

Embodiment 93 is a method of determining a genotype of the plant of any one of embodiments 1 to 11, 21, 74, 78, 82, 83, or 89 to 91, comprising obtaining a sample of nucleic acids from said plant and detecting in said nucleic acids a plurality of polymorphisms.

Embodiment 94 is the method of embodiment 93, further comprising a step of storing the results of detecting the plurality of polymorphisms on a computer readable medium.

Embodiment 95 is a method for producing a seed of a variety derived from tomato variety SND-017, comprising the steps of: (a) crossing a tomato plant of variety SND-017 with a second tomato plant to form a fertilized tomato plant of variety SND-017; and (b) cultivating the fertilized tomato plant of variety SND-017 until it forms a seed.

Embodiment 96 is the method of embodiment 95 further comprising the steps of: (c) crossing a plant grown from the seed of step (b) with itself or a third tomato plant to form a second fertilized tomato plant of variety SND-017, (d) cultivating the second fertilized tomato plant of variety SND-017 until it forms an additional seed; (e) growing said additional seed of step (d) to yield a third tomato plant of variety SND-017; and optionally (f) repeating the crossing and growing steps of (c) and (e) to generate additional tomato plants of variety SND-017.

Embodiment 97 is the method of embodiment 95 or 96, wherein the second tomato plant is of an inbred tomato variety.

Embodiment 98 is a plant comprising the scion or rootstock of embodiment 23 or 76.

Embodiment 99 is a method for producing a tomato fruit, the method comprising growing in a field or an area of cultivation a plant according to any one of embodiments 74, 78, 82, 83, or 89 to 91 or a seed or seedling thereof to produce a plant and cultivating the plant to produce a tomato fruit.

Embodiment 100 is the method of embodiment 99, wherein the method further comprises harvesting the tomato fruit from the plant.

Embodiment 102 is a food or feed product comprising a plant part of any one of embodiments 22 to 24.

Embodiment 103 is a food or feed product comprising a plant part of any one of embodiments 75 to 77.

EXAMPLES

The following examples are offered to illustrate, but not to limit, the claimed invention.

Example 1. Materials and Methods

Oligonucleotide design: upstream region targeting. Oligonucleotide pairs were designed to target the SlFSR gene in Brandywine and Micro Tom tomatoes. A Perl script was written that uses the gene sequence and offset coordinates from the transcriptional start site (TSS) and predicted TATA box (if found) to create a specific density of 25mer targets with a GC content of greater than 30%. Oligonucleotides were designed to implement two targeting strategies. The oligonucleotides used are listed in Table 1 as SEQ ID NOs:1-82. These oligonucleotides are homologous to portions of the transcriptional regulatory region within 1 kB upstream of the SlFSR translational start site (ATG), with the oligonucleotides of SEQ ID NOs: 41-82 targeting a region within 0.5 kB upstream of the SlFSR translational start site and the oligonucleotides of SEQ ID NOs: 1-40 targeting a region >5 kB to 1 kB upstream of the start site. In one strategy, oligonucleotides SEQ ID NOs: 1-82 were used (1 kB target region). In the other strategy, oligonucleotides SEQ ID NOs 41-82 were used (0.5 kB target region).

Oligonucleotide design: individual oligo pairs. For targeting a specific 25 nucleotide region of the genome, a double stranded modified DNA construct is synthesized. The duplex consists of two individual 24 nucleotide DNA strands having 100% homology to the genomic target region with 3' overhangs. Furthermore, the nucleotide at the 3' end of each strand is synthesized with a 2' O-methyl group. When the individual strands are annealed together, the duplex resembles a substrate for the RNA directed DNA methylation (RdDm) machinery of the plant.

Preparation of oligonucleotide solutions. Oligonucleotides were synthesized by commercial providers in 96-well plates. Pooled stocks for each oligo plate were made by taking 20 μL of a 500 μM stock from each well of that plate and combining these in a 2 mL tube. Afterwards, each pooled stock was combined in a 12 mL sterile falcon tube, mixed by pipetting, and briefly centrifuged to collect all contents. This pooled oligo mix was then pipetted into two eight-well PCR strip tubes and spun down. Tubes were placed in a PTC-200 Thermal cycler at 95° C. for 1 minute to denature the oligonucleotide complexes, and then cooled at room temperature for 10 minutes. The contents of the strip tubes were again combined in a fresh sterile 12 mL falcon tube, mixed by pipetting and centrifuged briefly to collect contents.

Treatment of Brandywine and Micro Tom tomato seeds and plant growth. Tomato seeds were fully submerged in a solution of oligonucleotides as described above and allowed to germinate at room temperature (around 20° C.) in the dark. After radicles had emerged, seeds were individually planted in soil and grown to approximately 4 inch high seedlings. Plants were transplanted into trade 5 gallon pots in a greenhouse facility, and tomato fruits were harvested as the fruits reached the breaker stage of fruit development. As the varieties have an indeterminate growth pattern, harvest of individual fruits continued for approximately 5 weeks. Individual fruits were harvested and tracked. Greenhouse temperature was maintained to a maximum of 77° F. and a minimum of 65° F. Plants were hand watered when surface of soil was dry. Light was provided for 16 hours per day with a combination of natural sunlight, high pressure sodium lights, and metal halide lights. A 20-20-20 (N-P-K) liquid fertilizer was applied weekly. Pesticides were applied as needed.

Tomato fruit shelf life measurements. Tomato shelf life was measured using a non-destructive penetrometer to assay fruit firmness, which does not penetrate the fruit but indicates how much the surface of the fruit yields or flexes at a given pressure and set measuring distance. The device used to measure fruit firmness in the experiments described herein was an HPE III Fff hardness tester, available from Bareiss. The resulting measurement can be represented as a quotient value (i.e., the relationship between the pressure and measuring distance) and shown on a scale of 0 to 100. Typically, tomato fruits lose firmness over time, eventually becoming too soft to assay further. A hard fruit at or before harvest at the breaker stage can measure a reading of about 60-80 though, in some instances, such fruits can measure a reading as low as 30-50. A very soft fruit measures a reading of about 10-15 using the HPE III Fff hardness tester. This point is a convenient assay end point, and can be used to quantify "mean survival time," or the time between tomato harvest and the first time the tomato is too soft to assay further, for individual fruits as well as populations of fruits from treated and untreated controls.

Bisulfite library preparation and sequencing. Bisulfite conversion was performed with the EZ DNA Methylation Gold kit (Zymo, Irvine, CA, USA), DNA was fragmented by Covaris, and library preparation was performed using the Accel-NGS Methyl-Seq kit (Swift Biosciences, Ann Arbor, MI, USA). An approximately 0.5% unmethylated lambda DNA spike-in was used as a bisulfite conversion rate control and for downstream bioinformatics.

Sequencing libraries were validated using the Agilent Tapestation 4200 (Agilent Technologies, Palo Alto, CA, USA), and quantified using a Qubit 2.0 Fluorometer (Invitrogen, Carlsbad, CA) as well as by quantitative PCR (Applied Biosystems, Carlsbad, CA, USA). The sequencing libraries were multiplexed and sequenced on the Illumina HiSeq instrument (4000 or equivalent) according to manufacturer's instructions. The samples were sequenced using a 2×150 Paired End (PE) configuration.

Differential methylation analysis. Bowtie indexes were created from C-to-T and G-to-A converted references of the genome using the 'genome_preparation' command of the bismark pipeline (Krueger and Andrews, 2011, Bioinformatics 27(11):1571-1572; bioinformatics.babraham.ac.uk/projects/bismark/). Reads were quality trimmed using Trimgalore (bioinformatics.babraham.ac.uk/projects/trim_galore/), aligned to the converted references using bismark, and methylation status was called from mapped reads using the 'bismark_methylation_extractor' command using the '--cytosine_report,' '--counts,' and '-CX' flags. CX-report files for each sample were processed for differential methylation analyses.

Methylome Analysis: DNA was extracted from the plant leaf using Zymo directzol plant DNA extraction kit. Once the DNA was extracted, an lsk-110 nanopore library was prepared. Briefly, DNA was end-repaired and then adapters were annealed to the DNA molecules that enable motor proteins to sequence long-reads on a minion or gridion sequencing device. DNA sequencing was carried out on an Oxford Nanopore R9 flow cell with adaptive sampling for genes of interest, optionally using a reference genome annotation. Each sample was processed through the Oxford Nanopore research tool "Megalodon" to determine whether each sequenced cytosine was methylated or unmethylated. These individual sequenced cytosines were aggregated by their position in the genome. The extent of methylation was computed for each cytosine in the genome (e.g. 80% of a specific cytosine are methylated) and for the overall genomic sequence (e.g. 5% of the genomic cytosines are methylated across the whole genome). Treated plants were compared with a control to quantify the increase in methylation.

Obtaining the plant genome: The target plant genome can be sequenced by any number of available methods and equipment. Some of the sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif), as described below. In addition to the single molecule sequencing performed using sequencing-by-synthesis of Helicos Biosciences, other single molecule sequencing technologies are encompassed by the method and include the SMRT™ technology of Pacific Biosciences, the Ion Torrent™ technology, and nanopore sequencing being developed for example, by Oxford Nanopore Technologies. See also: Li, F. W., and A. Harkess. 2018. A guide to sequence your favorite plant genomes. Applications in Plant Sciences 6(3): e1030, which is incorporated herein by reference in its entirety for all purposes.

Figure 3:
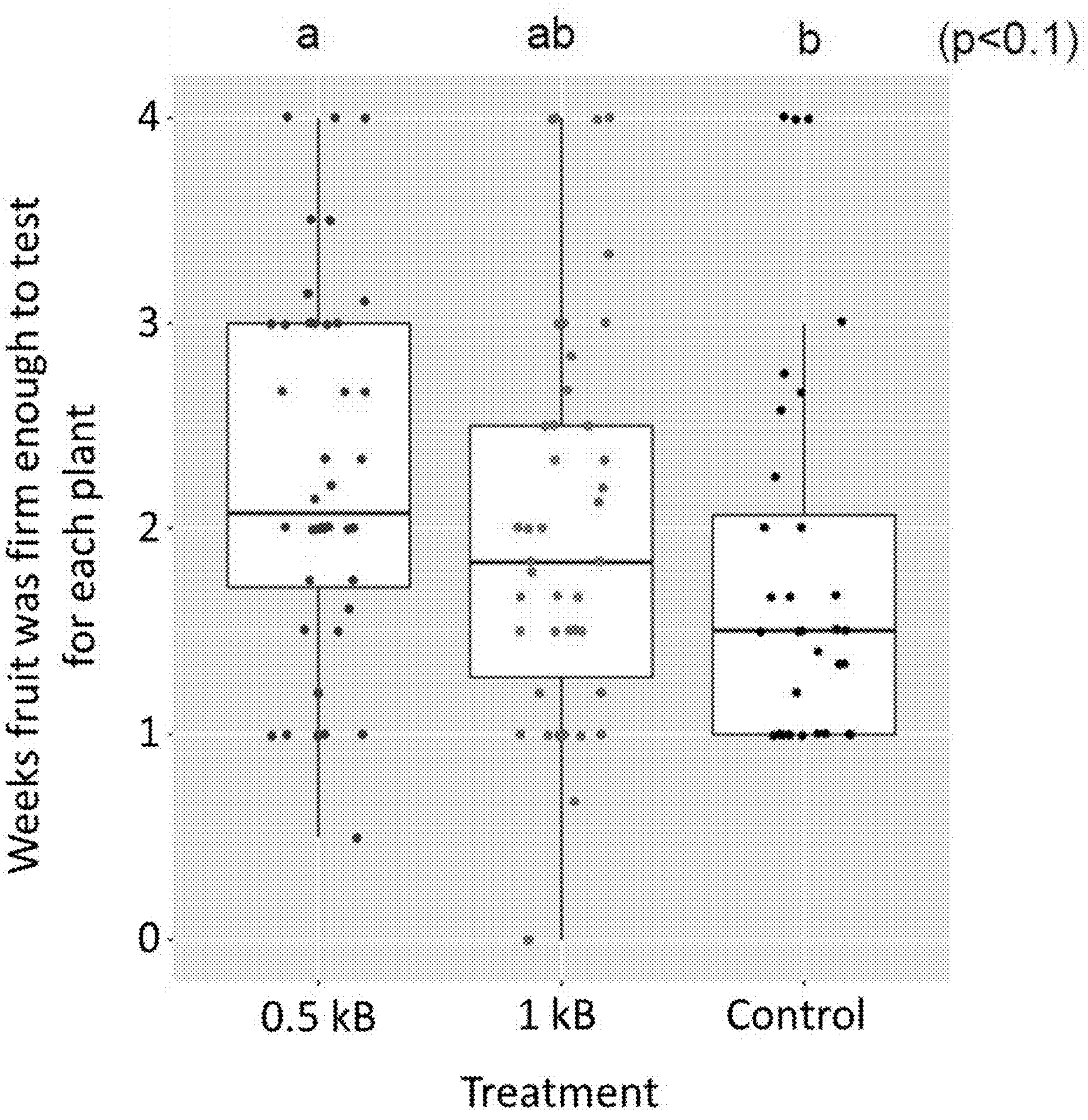
FIG. 3 shows tomato fruit shelf life for control-treated tomato plant population (right), 1 kB targeted tomato plant population (middle), and 0.5 kB targeted tomato plant population (left), according to aspects of this disclosure. Each dot represents the mean shelf life (or the number of weeks where the fruit was fresh and firm enough to be assayed with a non-destructive penetrometer) of 5-10 tomato fruits produced from one tomato plant in the respective tomato plant population. Bars show the upper and lower quartiles of the data for each population, and the horizontal lines show the average of the data for each population. Statistical significance groups (p<0.1, Tukey's method) are shown on the top.

Example 2. Extended Brandywine Tomato Fruit Shelf Life and Identification of Extended Shelf Life Clones The mean shelf life for each Brandywine plant in the 1 kB treated, 0.5 kB treated, and control populations were quantified (FIG. 3). Each plant produced 5 to 10 fruits over the course of the experiment, and the data represent the average shelf life of those fruits. Shelf life is defined here as the number of weeks where the fruit was fresh and firm enough to be assayed with a fruit firmness tester device (non-destructive penetrometer). The statistical significance ($p<0.1$ for the 0.5 kB versus control) of the population shows that the treatment is extending shelf life by approximately 4 days on average (FIG. 3).

Figure 4:
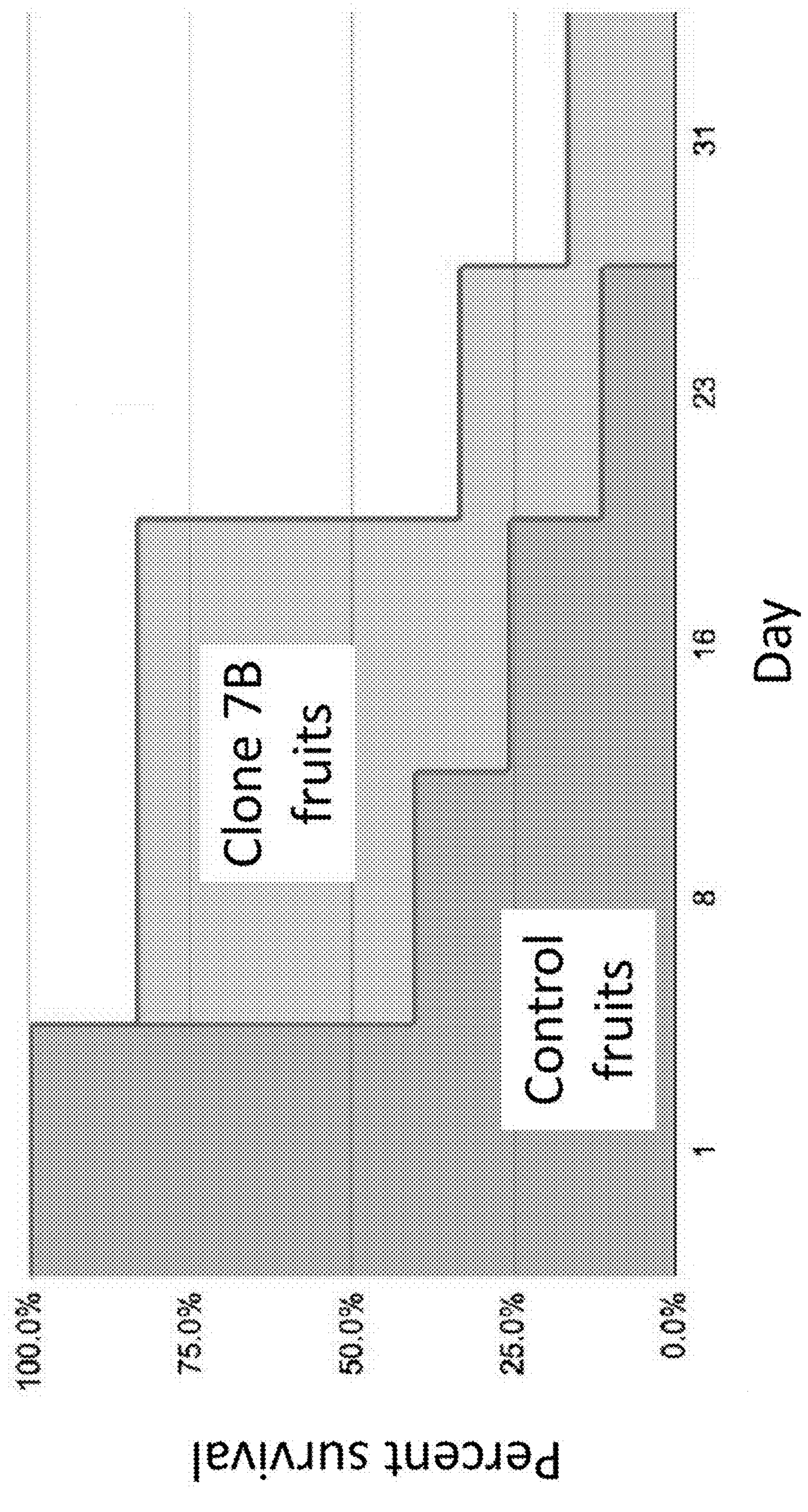
FIG. 4 shows a survival curve for tomato fruits from control-treated tomato plants (n>100 tomato fruits; bottom line) and clone 7B tomato plants (n=6 tomato fruits; top line), according to aspects of this disclosure. Data shown are the percentage of tomato fruits surviving (i.e., the tomato fruits that are fresh and firm enough to be assayed with a non-destructive penetrometer) over time.

Individual plants (clones) with enhanced shelf life compared to the treated population were identified. The clones are listed in Table 2, below, along with differences in mass (water weight) and firmness for fruits from the clones and fruits from control (i.e., unmodified) plants. Clone 17 is referred to in the disclosure above as SND-017. These values were determined by weight fruits from each clone (n>10 fruits each) and measuring firmness at harvest and one week post-harvest. Values are represented as a percentage decrease in mass/firmness. Statistical significance as determined by pairwise Student's t test is noted. For one of the clones (clone 7B), a survival curve analysis showed that the percentage of fruits 'surviving' over time was increased relative to an untreated clone (FIG. 4).

TABLE 2

Tomato fruit measurements in extended shelf life clones.

| | Control | Clone 55 | Clone 7B | Clone 17 (SND-017) |
|---|---|---|---|---|
| Decrease in mass | 11.2% | 8.6% | 6.8%* | 5.2%** |
| Decrease in firmness | 31.90% | 14.20%** | 13.60%* | 14.10%* |

Statistical significance: *$p < 0.1$; **$p < 0.01$.

Example 4. Hypermethylation in Targeted Area

Figure 5:
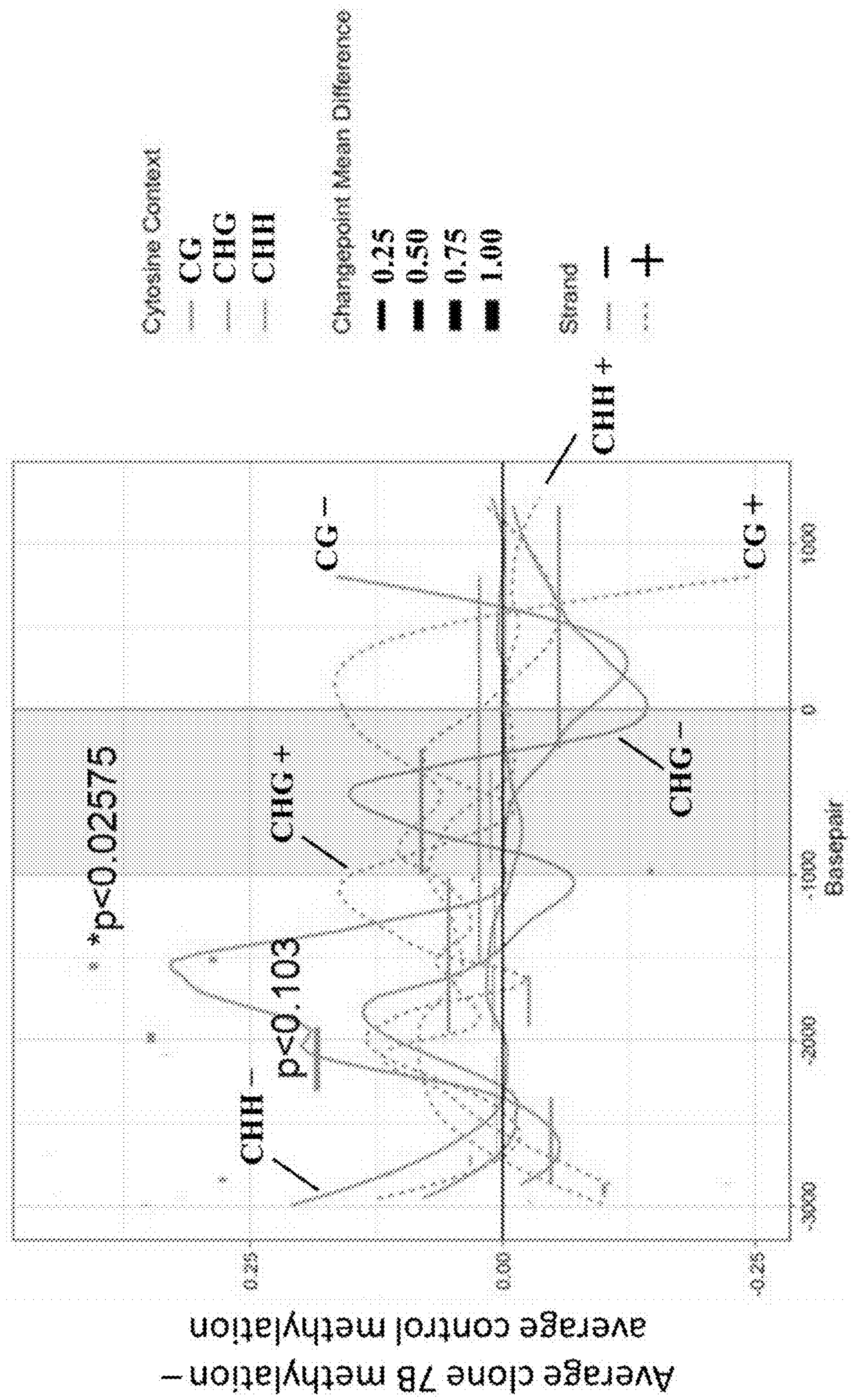
FIG. 5 shows a changepoint analysis of the difference in cytosine methylation between clone 7B tomato plants and control tomato plants, according to aspects of this disclosure. The x-axis shows the nucleotide position relative to the translation start site of the SlFSR gene (position 0). The y-axis shows the difference between methylation at each locus in clone 7B plants and control-treated plants. Values above zero indicate increased methylation in clone 7B plants relative to control plants, and values below zero indicate decreased methylation in clone 7B plants relative to control plants. Cytosine context is indicated as CG, cytosine-guanine; CHG, cytosine-(adenine, cytosine, or thymine)-guanine; or CHH, cytosine-(adenine, cytosine, or thymine)-(adenine, cytosine, or thymine).

Whole genome bisulfite sequencing (WGBS) was performed on clone 7B as well as several control plants. Differences between 7B and control plants at the target SlFSR locus were analyzed. Changepoint analysis was used to quantify the difference between 7B and control methylation by nucleotide position (FIG. 5). A significant increase in methylation was observed in the upstream region, particularly in CG contexts.

Example 5. Brandywine Generation 2 Testing

Figure 6A:
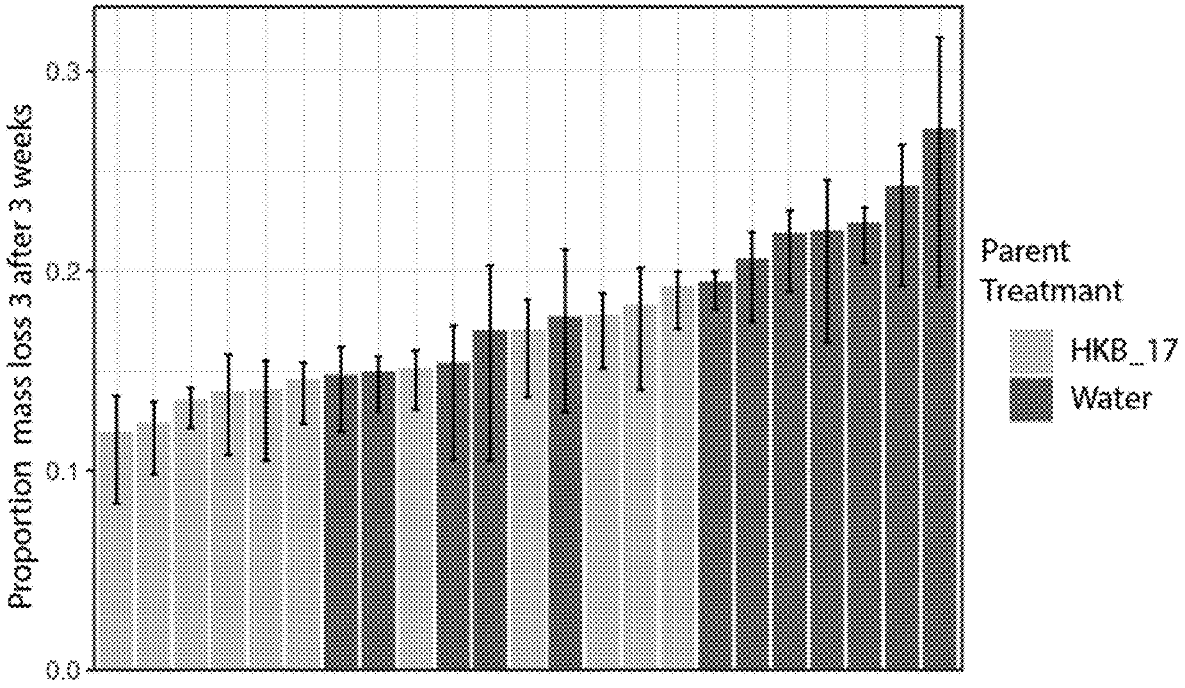
FIGS. 6A-6D show a comparison of mass and methylation between clone 17 (also referred to herein as SND-017) tomatoes and control tomatoes, according to aspects of this disclosure.
Figure 6B:
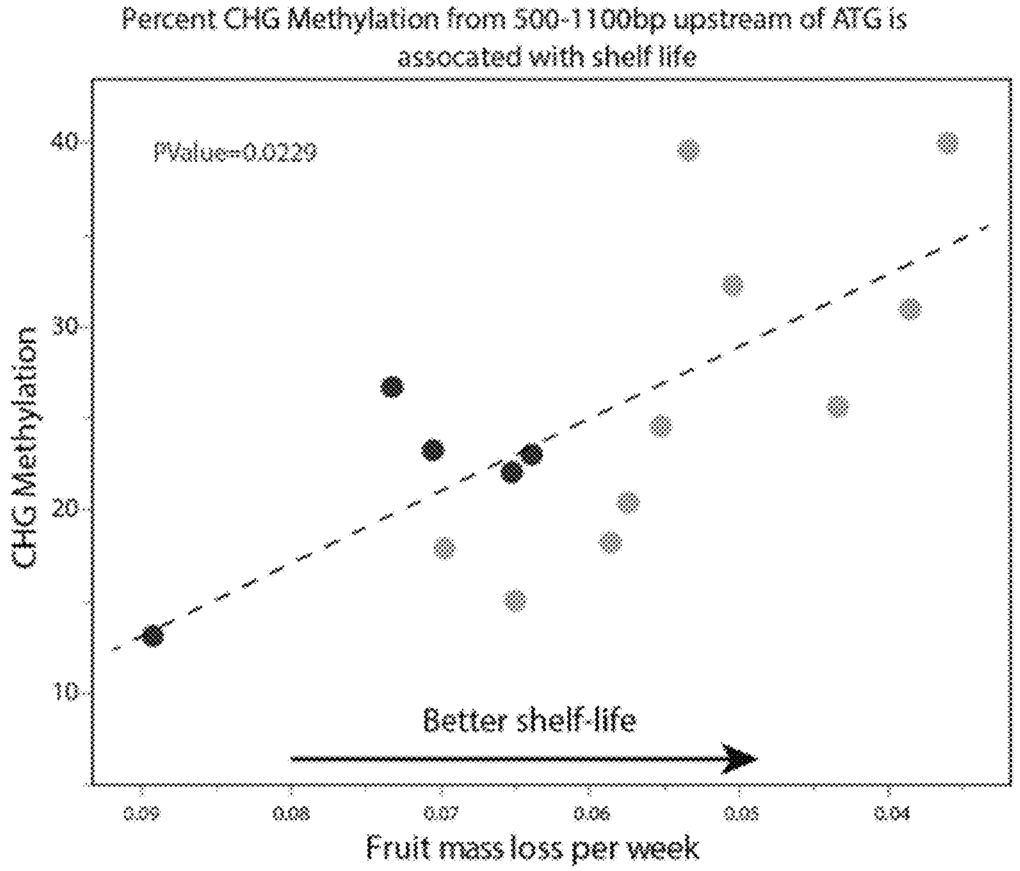
Figure 6C:
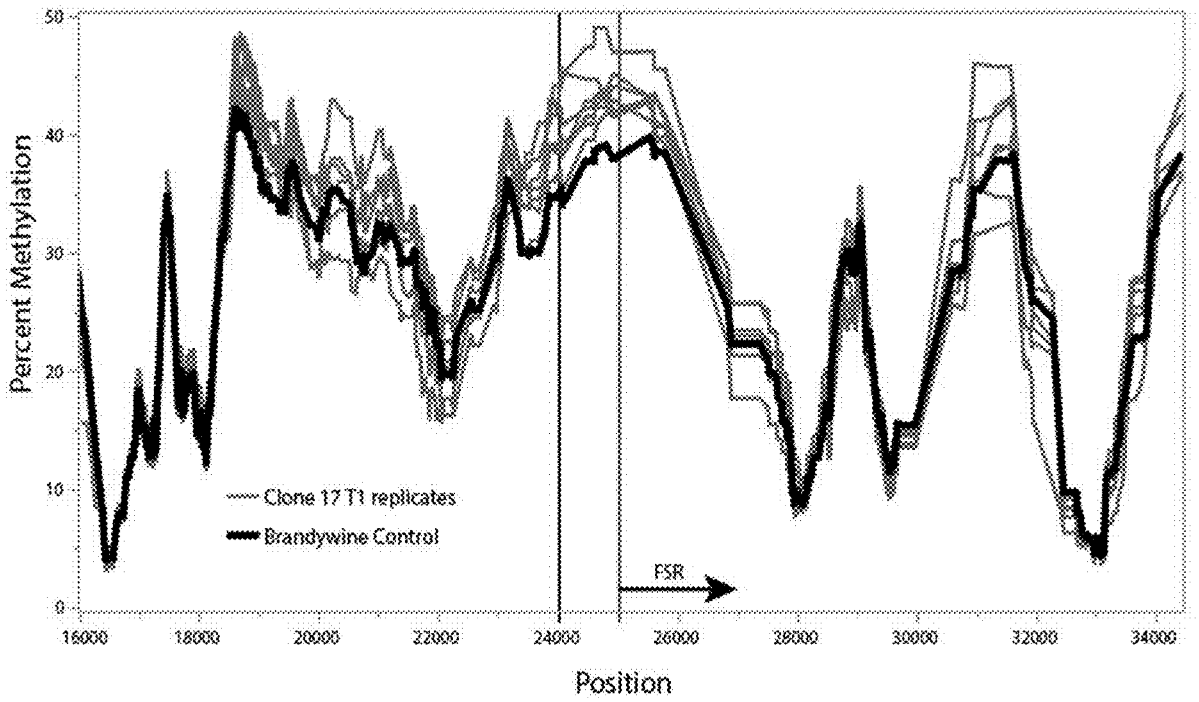
Figure 6D:
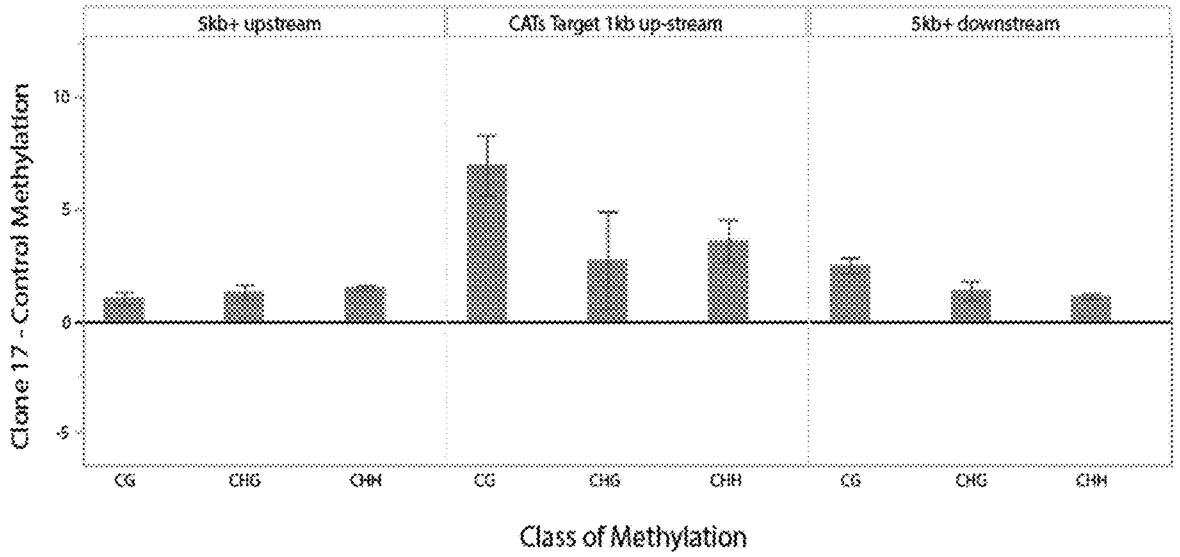

Seeds from clone 17 (SND-017) were harvested from the first-generation (TO) of plants and planted in a greenhouse in accordance with the procedure described in Example 1, except that TO seeds were were fully submerged in a water solution and tomatoes were harvested over a 12 week period once the fruits reached the breaker stage. 90 second-generation (T1) fruits from 12 offspring from this plant were harvested and assayed for shelf life. After three weeks post-harvest there was a significant increase in the proportion of starting weight remaining in the treated lines relative to control ($p=0.0014$, 15.6% vs. 19.6%, FIG. 6A). Additionally, a methylome analysis was obtained which showed that treated plants had significant increases in CHG methylation in the 500 to 1.1 kb up-stream of the transcription start site (FIG. 6B), overall percent methylation in the SlFSR gene and surrounding area (FIG. 6C), and CG, CHG, and CHH methylation within 5 kb up-stream and downstream of the transcription start site (FIG. 6D). A portion of the TO seeds were submerged in oligonucleotide solutions instead of water (as described above) and planted in the greenhouse to examine the impact of repeat seed treatment (data not shown).

Example 6. Brandywine Field Trials

Seeds from Clone 17 (SND-017) were harvested from the first-generation (TO) of plants and planted in a greenhouse. After 40-50 days of growth, the tomato plants were transferred to raised fumigated beds in an outdoor field in Immokalee, Florida. Plants were spaced at 1 row/bed with 2 feet of spacing between plants. Beds were 32 inches wide with a distance of 6 feet between centers of adjacent beds. Preplant fertilizer was applied at about 300-80-275 lb/acre of N, P, and K respectively at bed pressing on bed tops in a single band 3 inches deep and 4 inches away from transplants. Water was applied as a single drip tape per bed at a rate of 0.35 gal/hr with emitters 12 inches apart and 3 irrigation cycles of 1 hour per week for a total volume of 2500 gal/acre/day. Tomatoes were harvested between weeks 10 and 16 following transfer to the field with a yield ranging from 20.7 ton/acre.

Example 7. Extended Micro Tom Fruit Shelf Life

Figure 7:
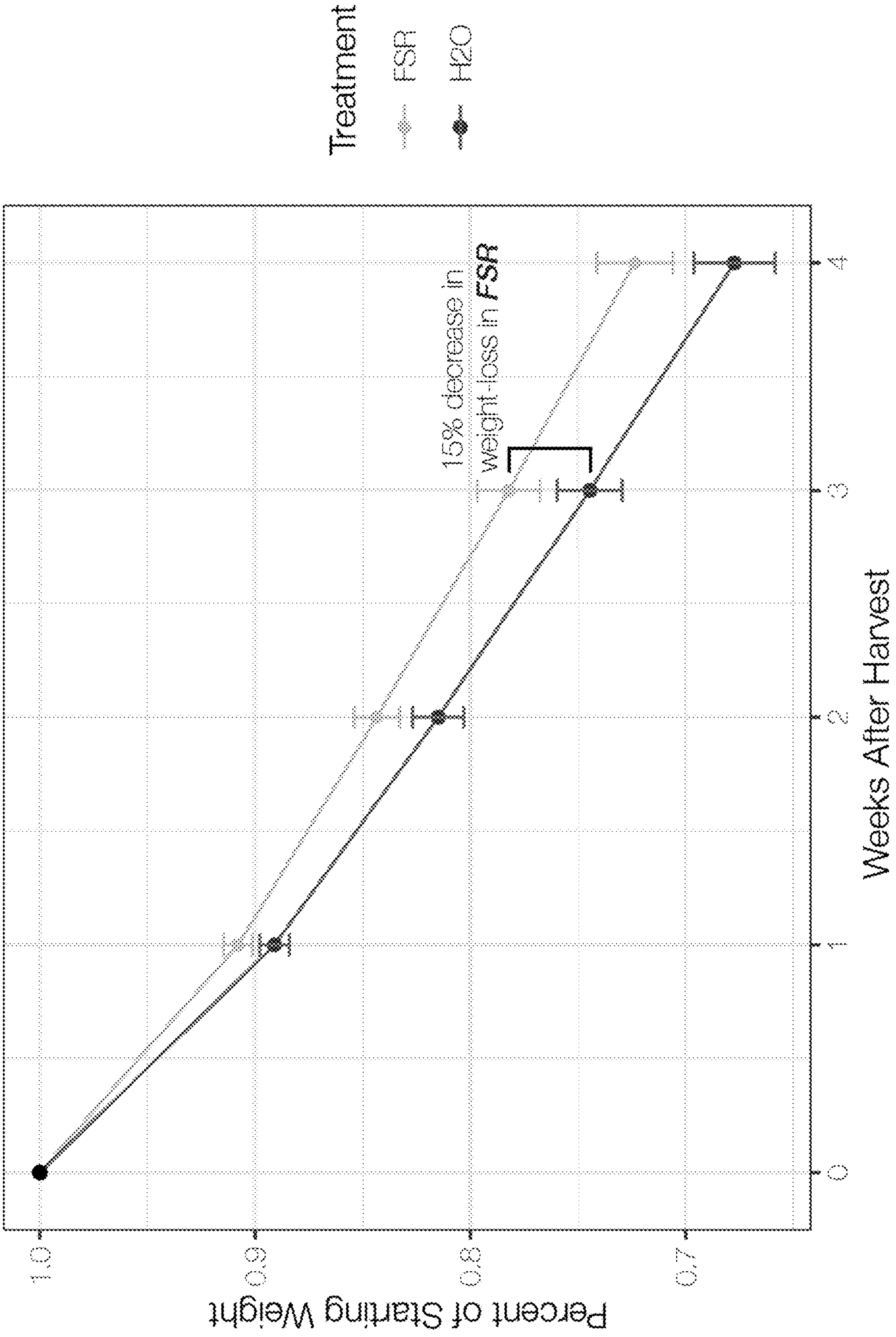
FIG. 7 shows weight loss over four weeks in Micro Tom tomatoes treated with oligonucleotides vs. water, according to aspects of this disclosure.

In order to test the efficacy of this approach across other varieties of tomato, a similar experiment was performed in *Solanum lycopersicum* var. "Micro Tom". Plants derived from seeds treated with SlFSR oligonucleotides had significantly less weight loss at 1 (p=0.0164, 10.1% vs. 9.2%), 2 (p=0.0154, 18.5% vs. 15.6%), 3 (p=0.0149, 25.5% vs. 21.7%) and 4 (p=0.0148, 32.3% vs. 27.6%) weeks post harvesting (FIG. 7).

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A modified tomato plant comprising an introduced modification comprising hypermethylation of genomic DNA at a *Solanum lycopersicum* fruit shelf-life regulator (SlFSR) gene or a transcription regulatory region thereof, wherein the hypermethylation is within a 1 kb region upstream of the translation start site of the SlFSR gene.

2. The modified tomato plant of claim 1, wherein the introduced modification is heritable.

3. The modified tomato plant of claim 1, wherein the modified tomato plant has a reduced expression level of a gene product encoded by the SlFSR gene, wherein the gene product is an mRNA transcript or a protein.

4. The modified tomato plant of claim 3, wherein the expression level of the gene product is reduced relative to the expression level of the gene product encoded by the SlFSR gene in an unmodified tomato plant.

5. The modified tomato plant of claim 1, wherein the modified tomato plant is of an heirloom variety.

6. The modified tomato plant of claim 1, wherein the modified tomato plant is of a Brandywine variety.

7. A modified tomato plant, wherein the modified tomato plant is an offspring of the modified tomato plant of claim 1.

8. A modified tomato fruit produced by the modified tomato plant of claim 1.

9. The modified tomato fruit of claim 8, wherein the modified tomato fruit has an extended shelf life relative to a tomato fruit produced from an unmodified tomato plant.

10. The modified tomato fruit of claim 8, wherein the modified tomato fruit retains an increased degree of firmness relative to an unmodified tomato fruit harvested at the same time at least 7 days after harvesting.

11. The modified tomato fruit of claim 8, wherein the modified tomato fruit has increased water content relative to an unmodified tomato fruit harvested at the same time at least 7 days after harvesting.

12. A modified tomato seed produced by the modified tomato plant of claim 1, comprising an introduced modification comprising hypermethylation of genomic DNA at a *Solanum lycopersicum* fruit shelf-life regulator (SlFSR) gene or a transcription regulatory region thereof, wherein the hypermethylation is within a 1 kb region upstream of the translation start site of the SlFSR gene.

13. A plant produced by growing the modified tomato seed of claim 12.

14. A method for producing a modified tomato fruit, the method comprising growing in a field or in an area of cultivation a modified tomato plant of claim 1 or a seed or seedling thereof to produce a modified tomato plant and cultivating the modified tomato plant to produce a modified tomato fruit.

15. The modified tomato plant of claim 1, wherein the hypermethylation is within a 0.5 kb region upstream of the translation start site of the SlFSR gene.

16. The modified tomato plant of claim 3, wherein the gene product is a mRNA transcript.

17. The modified tomato plant of claim 3, wherein the gene product is a protein.

18. The modified tomato plant of claim 1, wherein the modified tomato plant is of a Micro Tom variety.

19. The modified tomato fruit of claim 8, wherein the modified tomato fruit retains at least a pre-determined minimum degree of firmness for at least 14 days.

20. The modified tomato fruit of claim 8, wherein the modified tomato fruit retains at least a pre-determined minimum degree of firmness for at least 1.3 times as long as an unmodified tomato fruit.

21. The modified tomato fruit of claim 8, wherein the modified tomato fruit further comprises a coating that reduces ethylene release from the modified tomato fruit or absorbs ethylene released from the modified tomato fruit.

22. The modified tomato fruit of claim 8, wherein the modified tomato fruit is stored in a climate-controlled environment at a temperature between about 8° C. and about 24° C.

23. A plant part of the modified tomato plant of claim 1, comprising an introduced modification comprising hypermethylation of genomic DNA at a *Solanum lycopersicum* fruit shelf-life regulator (SlFSR) gene or a transcription regulatory region thereof, wherein the hypermethylation is within a 1 kb region upstream of the translation start site of the SlFSR gene.

24. The plant part of claim 23, wherein the plant part is a leaf, pollen, an ovule, a fruit, a scion, a rootstock, or a cell.

25. The plant part of claim 23, wherein the plant part is a fruit.

26. An isolated or cultured cell of the modified tomato plant of claim 1.

27. The isolated or cultured cell of claim 26, wherein the cell is from an embryo, a meristem, a cotyledon, a pollen, a leaf, an anther, a root, a root tip, a pistil, a flower, a seed, and/or a stalk, optionally wherein the cell is a protoplast.

28. A population of cells comprising a plurality of the isolated or cultured cells of claim 26.

29. A method for growing a modified tomato plant, the method comprising growing in a field or in an area of cultivation a modified tomato plant of claim 1 or a seed or seedling thereof.

30. The method of claim 14, wherein the method further comprises harvesting the modified tomato fruit from the modified tomato plant.

31. The modified tomato plant of claim 1, wherein the modified tomato plant comprises one or more transgenes and/or other modifications to the genome sequence that contribute to a desired phenotype to the modified tomato plant.

* * * * *

SEQUENCE LISTING

```
Sequence total quantity: 83
SEQ ID NO: 1           moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl guanine
SEQUENCE: 1
ttcatcctta tcagaggtct tcgg                                24

SEQ ID NO: 2           moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl adenine
SEQUENCE: 2
cgaagacctc tgataaggat gaaa                                24

SEQ ID NO: 3           moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl uracil
SEQUENCE: 3
tcgagctctg ggtatggaca aaat                                24

SEQ ID NO: 4           moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl adenine
SEQUENCE: 4
ttttgtccat acccagagct cgaa                                24

SEQ ID NO: 5           moltype = DNA  length = 24
FEATURE                Location/Qualifiers
source                 1..24
                       mol_type = other DNA
```

-continued

```
                      organism = synthetic construct
modified_base         24
                      mod_base = OTHER
                      note = 2'-O-methyl uracil
SEQUENCE: 5
gctactcctg aatgggccct atat                                        24

SEQ ID NO: 6          moltype = DNA  length = 24
FEATURE               Location/Qualifiers
source                1..24
                      mol_type = other DNA
                      organism = synthetic construct
modified_base         24
                      mod_base = OTHER
                      note = 2'-O-methyl guanine
SEQUENCE: 6
tatagggccc attcaggagt agcg                                        24

SEQ ID NO: 7          moltype = DNA  length = 24
FEATURE               Location/Qualifiers
source                1..24
                      mol_type = other DNA
                      organism = synthetic construct
modified_base         24
                      mod_base = OTHER
                      note = 2'-O-methyl guanine
SEQUENCE: 7
gtgcgccatc caaatttaat cggg                                        24

SEQ ID NO: 8          moltype = DNA  length = 24
FEATURE               Location/Qualifiers
source                1..24
                      mol_type = other DNA
                      organism = synthetic construct
modified_base         24
                      mod_base = OTHER
                      note = 2'-O-methyl uracil
SEQUENCE: 8
ccgattaaat ttggatggcg cact                                        24

SEQ ID NO: 9          moltype = DNA  length = 24
FEATURE               Location/Qualifiers
source                1..24
                      mol_type = other DNA
                      organism = synthetic construct
modified_base         24
                      mod_base = OTHER
                      note = 2'-O-methyl guanine
SEQUENCE: 9
ctctaatatg gtctccgaac aacg                                        24

SEQ ID NO: 10         moltype = DNA  length = 24
FEATURE               Location/Qualifiers
source                1..24
                      mol_type = other DNA
                      organism = synthetic construct
modified_base         24
                      mod_base = OTHER
                      note = 2'-O-methyl cytosine
SEQUENCE: 10
gttgttcgga gaccatatta gagc                                        24

SEQ ID NO: 11         moltype = DNA  length = 24
FEATURE               Location/Qualifiers
source                1..24
                      mol_type = other DNA
                      organism = synthetic construct
modified_base         24
                      mod_base = OTHER
                      note = 2'-O-methyl adenine
SEQUENCE: 11
ataaaaaaaa aaactgttca ccaa                                        24

SEQ ID NO: 12         moltype = DNA  length = 24
FEATURE               Location/Qualifiers
source                1..24
                      mol_type = other DNA
                      organism = synthetic construct
modified_base         24
```

```
                        mod_base = OTHER
                        note = 2'-O-methyl guanine
SEQUENCE: 12
tggtgaacag tttttttttt tatg                                          24

SEQ ID NO: 13           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl guanine
SEQUENCE: 13
cttttggtgg ttagcaaaat ttgg                                          24

SEQ ID NO: 14           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl guanine
SEQUENCE: 14
caaattttgc taaccaccaa aagg                                          24

SEQ ID NO: 15           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl uracil
SEQUENCE: 15
aatcaattta cttgatgaag ttct                                          24

SEQ ID NO: 16           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl adenine
SEQUENCE: 16
gaacttcatc aagtaaattg atta                                          24

SEQ ID NO: 17           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl cytosine
SEQUENCE: 17
taaagtaata ttattccaca cacc                                          24

SEQ ID NO: 18           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl guanine
SEQUENCE: 18
gtgtgtggaa taatattact ttag                                          24

SEQ ID NO: 19           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl cytosine
```

-continued

```
SEQUENCE: 19
aagagtattc aaatttgaat tccc                                              24

SEQ ID NO: 20          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl uracil
SEQUENCE: 20
ggaattcaaa tttgaatact cttt                                              24

SEQ ID NO: 21          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl adenine
SEQUENCE: 21
tcaaatagaa aaaagaatga aaaa                                              24

SEQ ID NO: 22          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl adenine
SEQUENCE: 22
ttttcattct tttttctatt tgaa                                              24

SEQ ID NO: 23          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl adenine
SEQUENCE: 23
aggttaatta cttaatatga aaaa                                              24

SEQ ID NO: 24          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl guanine
SEQUENCE: 24
ttttcatatt aagtaattaa cctg                                              24

SEQ ID NO: 25          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl guanine
SEQUENCE: 25
ctgaattaga tttcaagctt atag                                              24

SEQ ID NO: 26          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl uracil
SEQUENCE: 26
tataagcttg aaatctaatt cagt                                              24
```

```
SEQ ID NO: 27          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl adenine
SEQUENCE: 27
gactaggtcc ttatagtaca tgca                                          24

SEQ ID NO: 28          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl uracil
SEQUENCE: 28
gcatgtacta taaggaccta gtct                                          24

SEQ ID NO: 29          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl guanine
SEQUENCE: 29
gttaattaat ctaatatttt aggg                                          24

SEQ ID NO: 30          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl adenine
SEQUENCE: 30
cctaaaatat tagattaatt aaca                                          24

SEQ ID NO: 31          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl uracil
SEQUENCE: 31
gaatttatag agttctaact tggt                                          24

SEQ ID NO: 32          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl adenine
SEQUENCE: 32
ccaagttaga actctataaa ttca                                          24

SEQ ID NO: 33          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl cytosine
SEQUENCE: 33
catatagcta gagatcttca aatc                                          24

SEQ ID NO: 34          moltype = DNA  length = 24
```

-continued

```
FEATURE                 Location/Qualifiers
source                  1..24
                        mol_type = other DNA
                        organism = synthetic construct
modified_base           24
                        mod_base = OTHER
                        note = 2'-O-methyl guanine
SEQUENCE: 34
atttgaagat ctctagctat atgg                                          24

SEQ ID NO: 35           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl adenine
SEQUENCE: 35
aacaaacaat tttgtttgct aaca                                          24

SEQ ID NO: 36           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl uracil
SEQUENCE: 36
gttagcaaac aaaattgttt gttt                                          24

SEQ ID NO: 37           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl adenine
SEQUENCE: 37
aacagtaaga aagtaattgg gtaa                                          24

SEQ ID NO: 38           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl uracil
SEQUENCE: 38
tacccaatta ctttcttact gttt                                          24

SEQ ID NO: 39           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl uracil
SEQUENCE: 39
gagaatgtta aaatctctga ccat                                          24

SEQ ID NO: 40           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl cytosine
SEQUENCE: 40
tggtcagaga ttttaacatt ctcc                                          24

SEQ ID NO: 41           moltype = DNA  length = 24
FEATURE                 Location/Qualifiers
source                  1..24
```

```
                        mol_type = other DNA
                        organism = synthetic construct
modified_base           24
                        mod_base = OTHER
                        note = 2'-O-methyl adenine
SEQUENCE: 41
ttatttaaac gtttaagtta ttaa                                            24

SEQ ID NO: 42           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl guanine
SEQUENCE: 42
taataactta aacgtttaaa taag                                            24

SEQ ID NO: 43           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl uracil
SEQUENCE: 43
taaagcaatt ttttatttat ttat                                            24

SEQ ID NO: 44           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl uracil
SEQUENCE: 44
taaataaata aaaaattgct ttat                                            24

SEQ ID NO: 45           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl cytosine
SEQUENCE: 45
ttttgtttaa cacgactctt cacc                                            24

SEQ ID NO: 46           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl adenine
SEQUENCE: 46
gtgaagagtc gtgttaaaca aaaa                                            24

SEQ ID NO: 47           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl uracil
SEQUENCE: 47
gcagacctaa ttattttttt tcat                                            24

SEQ ID NO: 48           moltype = DNA  length = 24
FEATURE                 Location/Qualifiers
source                  1..24
                        mol_type = other DNA
                        organism = synthetic construct
```

-continued

```
modified_base         24
                      mod_base = OTHER
                      note = 2'-O-methyl guanine
SEQUENCE: 48
tgaaaaaaaa taattaggtc tgcg                                          24

SEQ ID NO: 49         moltype = DNA  length = 24
FEATURE               Location/Qualifiers
source                1..24
                      mol_type = other DNA
                      organism = synthetic construct
modified_base         24
                      mod_base = OTHER
                      note = 2'-O-methyl uracil
SEQUENCE: 49
gttcaagctt gtgaaatttc tttt                                          24

SEQ ID NO: 50         moltype = DNA  length = 24
FEATURE               Location/Qualifiers
source                1..24
                      mol_type = other DNA
                      organism = synthetic construct
modified_base         24
                      mod_base = OTHER
                      note = 2'-O-methyl uracil
SEQUENCE: 50
aaagaaattt cacaagcttg aact                                          24

SEQ ID NO: 51         moltype = DNA  length = 24
FEATURE               Location/Qualifiers
source                1..24
                      mol_type = other DNA
                      organism = synthetic construct
modified_base         24
                      mod_base = OTHER
                      note = 2'-O-methyl uracil
SEQUENCE: 51
gatactcctg atcaatctct actt                                          24

SEQ ID NO: 52         moltype = DNA  length = 24
FEATURE               Location/Qualifiers
source                1..24
                      mol_type = other DNA
                      organism = synthetic construct
modified_base         24
                      mod_base = OTHER
                      note = 2'-O-methyl adenine
SEQUENCE: 52
agtagagatt gatcaggagt atca                                          24

SEQ ID NO: 53         moltype = DNA  length = 24
FEATURE               Location/Qualifiers
source                1..24
                      mol_type = other DNA
                      organism = synthetic construct
modified_base         24
                      mod_base = OTHER
                      note = 2'-O-methyl uracil
SEQUENCE: 53
ctctggtact atattgaaat acat                                          24

SEQ ID NO: 54         moltype = DNA  length = 24
FEATURE               Location/Qualifiers
source                1..24
                      mol_type = other DNA
                      organism = synthetic construct
modified_base         24
                      mod_base = OTHER
                      note = 2'-O-methyl cytosine
SEQUENCE: 54
tgtatttcaa tatagtacca gagc                                          24

SEQ ID NO: 55         moltype = DNA  length = 24
FEATURE               Location/Qualifiers
source                1..24
                      mol_type = other DNA
                      organism = synthetic construct
modified_base         24
                      mod_base = OTHER
```

-continued

```
                        note = 2'-O-methyl adenine
SEQUENCE: 55
gaatatattc cagccgtata tata                                              24

SEQ ID NO: 56           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl guanine
SEQUENCE: 56
atatatacgg ctggaatata ttcg                                              24

SEQ ID NO: 57           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl cytosine
SEQUENCE: 57
tagtagtact ctttcactaa tccc                                              24

SEQ ID NO: 58           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl adenine
SEQUENCE: 58
ggattagtga aagagtacta ctaa                                              24

SEQ ID NO: 59           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl adenine
SEQUENCE: 59
ctctctttc ttggattact taaa                                               24

SEQ ID NO: 60           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl adenine
SEQUENCE: 60
ttaagtaatc caagaaaaga gaga                                              24

SEQ ID NO: 61           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl adenine
SEQUENCE: 61
atatctttgc ttcatctata tata                                              24

SEQ ID NO: 62           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl guanine
SEQUENCE: 62
```

-continued

```
atatatagat gaagcaaaga tatg                                          24

SEQ ID NO: 63           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl cytosine
SEQUENCE: 63
aagatatatc tccagtctga ttac                                          24

SEQ ID NO: 64           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl adenine
SEQUENCE: 64
taatcagact ggagatatat ctta                                          24

SEQ ID NO: 65           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl adenine
SEQUENCE: 65
cattttcttc catatttttc ttca                                          24

SEQ ID NO: 66           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl adenine
SEQUENCE: 66
gaagaaaaat atggaagaaa atga                                          24

SEQ ID NO: 67           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl adenine
SEQUENCE: 67
acttacatgc acgtacataa aaca                                          24

SEQ ID NO: 68           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl uracil
SEQUENCE: 68
gttttatgta cgtgcatgta agtt                                          24

SEQ ID NO: 69           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl cytosine
SEQUENCE: 69
aaccttacat attttttaa ttcc                                           24
```

-continued

```
SEQ ID NO: 70          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl uracil
SEQUENCE: 70
gaattaaaaa aatatgtaag gttt                                          24

SEQ ID NO: 71          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl uracil
SEQUENCE: 71
tatatataat acttagtcat acat                                          24

SEQ ID NO: 72          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl adenine
SEQUENCE: 72
tgtatgacta agtattatat ataa                                          24

SEQ ID NO: 73          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl cytosine
SEQUENCE: 73
actccatcat gaaaaaggaa atcc                                          24

SEQ ID NO: 74          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl guanine
SEQUENCE: 74
gatttccttt ttcatgatgg agtg                                          24

SEQ ID NO: 75          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl cytosine
SEQUENCE: 75
atttcagtaa gacttgatct gatc                                          24

SEQ ID NO: 76          moltype = DNA  length = 24
FEATURE                Location/Qualifiers
source                 1..24
                       mol_type = other DNA
                       organism = synthetic construct
modified_base          24
                       mod_base = OTHER
                       note = 2'-O-methyl adenine
SEQUENCE: 76
atcagatcaa gtcttactga aata                                          24

SEQ ID NO: 77          moltype = DNA  length = 24
FEATURE                Location/Qualifiers
```

-continued

```
source                  1..24
                        mol_type = other DNA
                        organism = synthetic construct
modified_base           24
                        mod_base = OTHER
                        note = 2'-O-methyl guanine
SEQUENCE: 77
atcgtatagt ttagattcaa gttg                                        24

SEQ ID NO: 78           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl uracil
SEQUENCE: 78
aacttgaatc taaactatac gatt                                        24

SEQ ID NO: 79           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl uracil
SEQUENCE: 79
tcgttgcttc cattttattg tgtt                                        24

SEQ ID NO: 80           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl cytosine
SEQUENCE: 80
acacaataaa atggaagcaa cgac                                        24

SEQ ID NO: 81           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl guanine
SEQUENCE: 81
atcattatac atagtagagt caag                                        24

SEQ ID NO: 82           moltype = DNA  length = 24
FEATURE                 Location/Qualifiers
source                  1..24
                        mol_type = other DNA
                        organism = synthetic construct
modified_base           24
                        mod_base = OTHER
                        note = 2'-O-methyl adenine
SEQUENCE: 82
ttgactctac tatgtataat gata                                        24

SEQ ID NO: 83           moltype = DNA  length = 1290
FEATURE                 Location/Qualifiers
source                  1..1290
                        mol_type = genomic DNA
                        organism = Solanum lycopersicum
SEQUENCE: 83
atgaactcta caaccattcc cctccaaaac cctagttttt tcaacaactc tcaaagttct  60
ctagcaggag cactacaagg atgcattggg agccttgatg gagcatgttt ggagaaacta  120
ttacttcatt gtgcaagtgc cttagagaac aatgatgtaa ctttggctca acaagtcatg  180
tgggtgctca acaatttggc ttcttctaat ggagatccaa atcaaagact cacatcatgg  240
ttccttaggg cattaatttc aagggcttct agggtttatc ctaatgccac aaatttacat  300
ggaagtagta accttgaaag gagattaatg agtgtgactg agctagcagg gtatgtggat  360
ctcatcccat ggcatagatt tggattttgt gcatcaaata gtgttattta taaggccatt  420
gaaaggcaaa caaaagttca catattagat tttagtatca ctcattgtat gcaatggcca  480
actctcattg atgcaattgc taagaggcct gagggtcctc cttctctccg aatatcggtg  540
```

-continued

```
ccttcatgga gaccacaagt tcctccattg ctcaatgtgt caagtgaaga agttggccaa  600
cgtttggcaa atttcgcgaa atttagagat gttccttttg aattccatgt gattgaagac  660
ttgaactatg acatgttctt gagccaattg aatccttcaa ctcttcaaat tagagatgat  720
gaagctttgg ttgtgaattg ccaaaattgg ttaaggtact tacatgatga tgaacaaatt  780
aagggtgcac tttcgtctcg cgacatattt cttgataggg ttaaggattt aaacccttgt  840
attgtgacta ttgttgatga agattgtgat ttgggaaacc caactacttt aacatcaaga  900
atagccactt gttttaacta tctatggata ccttttgatg cattagagac atttttgcct  960
aaggatagta agcaaaggct agattatgaa gctgagattg gccacaaaat tgaaaacatt  1020
attggatttg aagggaacca aaggatagag agattagaga gttgcaacaa gttctcacaa  1080
aggatggaaa atagtggtta catgagtgta cctttttagtg aagaaacaat aaaggaagtc  1140
aagtcattgt tggatgaaca tgcaagtgga tggggcatga aaaaagagga acatgacatg  1200
cttgtattaa catggaaagg tcataactct gtctatgcaa catcttgggt catagtctca  1260
ccaccccata tggacatgag tagcttataa                                  1290
```